United States Patent
Sheridan et al.

(10) Patent No.: US 9,499,554 B2
(45) Date of Patent: Nov. 22, 2016

(54) ANTI-INFLUENZA COMPOSITIONS AND METHODS

(71) Applicant: BioCryst Pharmaceuticals, Inc., Durham, NC (US)

(72) Inventors: William P. Sheridan, Durham, NC (US); Shanta Bantia, Birmingham, AL (US); Pravin L. Kotian, Birmingham, AL (US); Yarlagadda S. Babu, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 14/890,719

(22) PCT Filed: May 14, 2014

(86) PCT No.: PCT/US2014/038000
§ 371 (c)(1),
(2) Date: Nov. 12, 2015

(87) PCT Pub. No.: WO2014/186465
PCT Pub. Date: Nov. 20, 2014

(65) Prior Publication Data
US 2016/0096842 A1   Apr. 7, 2016

Related U.S. Application Data

(60) Provisional application No. 61/823,133, filed on May 14, 2013, provisional application No. 61/823,135, filed on May 14, 2013.

(51) Int. Cl.
| | | |
|---|---|---|
| *A01N 43/90* | (2006.01) | |
| *A61K 31/519* | (2006.01) | |
| *C07D 487/00* | (2006.01) | |
| *C07D 487/04* | (2006.01) | |
| *C07D 471/04* | (2006.01) | |
| *A61K 31/13* | (2006.01) | |
| *A61K 45/06* | (2006.01) | |

(52) U.S. Cl.
CPC ............ *C07D 487/04* (2013.01); *A61K 31/13* (2013.01); *A61K 31/519* (2013.01); *A61K 45/06* (2013.01); *C07D 471/04* (2013.01)

(58) Field of Classification Search
None
See application file for complete search history.

(56) References Cited

U.S. PATENT DOCUMENTS

| 6,562,861 B1 | 5/2003 | Babu et al. |
| 2003/0181693 A1 | 9/2003 | Cook et al. |
| 2012/0077974 A1 | 3/2012 | Lindsay et al. |
| 2013/0023585 A1 | 1/2013 | Hilfinger et al. |

FOREIGN PATENT DOCUMENTS

WO   WO-2012051570 A1   4/2012

OTHER PUBLICATIONS

Gupta, SV, et al. Enhancing the Intestinal Membrane Permeability of Zanamivir: A Carrier Mediated Prodrug Approach. Molecular Pharmacology, vol. 8, No. 6, Dec. 5, 2011, pp. 2358-2367.
D'Souza, C., et al. Probing molecular leval interaction of oseltamivir with H5N1-NA and model membranes by molecular docking, multinuclear NMR and DSC methods. Biochimica et Biophysica Acta, vol. 1788, 2009, pp. 484-494.
Giorgi, ME, et al., Synthesis of oseltamivir conjugates with lactose analogs for inhibition studies on Trypanosoma cruzi trans-sialidase. ARKIVOC: Online Journal of Organic Chemistry, Jan. 2011, pp. 260-271.
International Search Report and Written Opinion for PCT/US14/38000 dated Sep. 18, 2014.

*Primary Examiner* — Jeffrey H Murray
(74) *Attorney, Agent, or Firm* — Dana M. Gordon; Foley Hoag LLP

(57) ABSTRACT

Disclosed are novel compounds comprising an imino-ribose derivative covalently linked to a carbocycle or heterocycle. Pharmaceutical compositions comprising the compounds of the invention are also described. Methods of inhibition, treatment and/or suppression of viral infections with the compounds of the invention are also described. The compositions or methods may optionally comprise one or more additional anti-viral agents.

24 Claims, 7 Drawing Sheets

US 9,499,554 B2

ANTI-INFLUENZA COMPOSITIONS AND METHODS

RELATED APPLICATIONS

This application is the U.S. national phase of International Patent Application No. PCT/US14/038000, filed May 14, 2014, which claims the benefit of priority to U.S. Provisional Patent Application No. 61/823,133, filed May 14, 2013; and U.S. Provisional Patent Application No. 61/823,135, filed May 14, 2013; both of which applications are hereby incorporated by reference in their entirety.

BACKGROUND

Viral diseases are responsible for both global pandemics and yearly seasonal epidemics, such as influenza. Outbreaks may be characterized by potentiated virulence and may occur suddenly, resulting in serious mortality. Importantly, viral diseases are not limited to humans. For example, influenza also affects livestock and birds, which may have significant impact on food supply in addition to increasing the risk of transmission to humans.

Influenza viruses contain viral RNA molecules enclosed within an envelope comprised of a matrix protein and a lipid bilayer. Embedded into the lipid membrane are glycoproteins known as HA (hemagglutinin) and NA (neuraminidase). HA is responsible for the binding of the virus to the host cell through sialic acid receptors, and NA acts to release virions from plasma membranes of the infected cells and allows the progeny virions to infect other cells spreading the infection. The HA and NA are also important in the immune response against the virus; antibodies against them may protect against infection. Neuraminidase is the target of many antivirals, such as oseltamivir, peramivir and zanamivir.

Within the interior of a virion, the genome of the influenza A virus has an RNA-dependent RNA polymerase, which is a heterotrimeric complex of three subunits (PA, PB1 and PB2). The RNA polymerase catalyzes viral RNA transcription and replication. Because transcription and replication of the virus depends on the activity of RNA polymerase, the enzyme is also a potential target for development of new anti-viral compounds, especially in light of the emergence of drug resistant viruses.

SUMMARY OF THE INVENTION

The invention provides compounds, methods and compositions for inhibition of viral neuraminidase and nucleic acid polymerases, and methods and compositions that are useful for treating, suppressing and/or preventing viral infections and conditions related to viral infections in subjects. The compounds of the invention are comprised of a neuraminidase inhibitor joined via a chemical linker to a nucleic acid polymerase inhibitor. When administered to a subject, the linker may be cleaved to release the neuraminidase inhibitor and the polymerase inhibitor.

The methods comprise administering to the subject a compound of formula I, or a pharmaceutically acceptable salt thereof, or a composition comprising a compound of formula I, or a pharmaceutically acceptable salt thereof. The compositions and/or methods may optionally comprise one or more additional anti-viral agents.

The present invention is based, in part, on the discovery that levels of viral titer in cells were markedly reduced upon treatment with a neuraminidase inhibitor in conjunction with a polymerase inhibitor, both of which are embodied within a compound of formula I. In addition to a neuraminidase inhibitor and a nucleic acid polymerase inhibitor, a compound of formula I further comprises a linker, which is covalently bound to each inhibitor moiety. One or both of the connections between the linker and inhibitor moieties may be cleaved following administration to the subject, thus releasing, e.g., the individual neuraminidase inhibitor and the nucleic acid polymerase inhibitor within the subject.

The present invention also provides methods for reducing viral titer in a bodily fluid or cell comprised of treating said fluid or cell with a compound of formula I.

In another embodiment, the present invention provides a method for inhibiting a viral RNA or DNA polymerase in a subject, comprising administration of an effective inhibitory amount of a compound of formula I, or a pharmaceutically acceptable salt thereof.

In another embodiment, the present invention provides a method for treating a subject suffering from an RNA viral infection which comprises administering to said patient an effective amount of a compound of formula I, or a pharmaceutically acceptable salt thereof.

In one embodiment, the bodily fluid is blood. In another embodiment, the bodily fluid is plasma. In still another embodiment, the bodily fluid is blood serum.

In one embodiment, the subject is a mammal. In another embodiment the subject is a human. In yet another embodiment, the subject is avian. In still another embodiment, the subject is a swine or pig.

These and other embodiments of the invention are further described in the following sections of the application, including the Detailed Description, Examples, Claims, and Figures.

DETAILED DESCRIPTION

Figure 1:
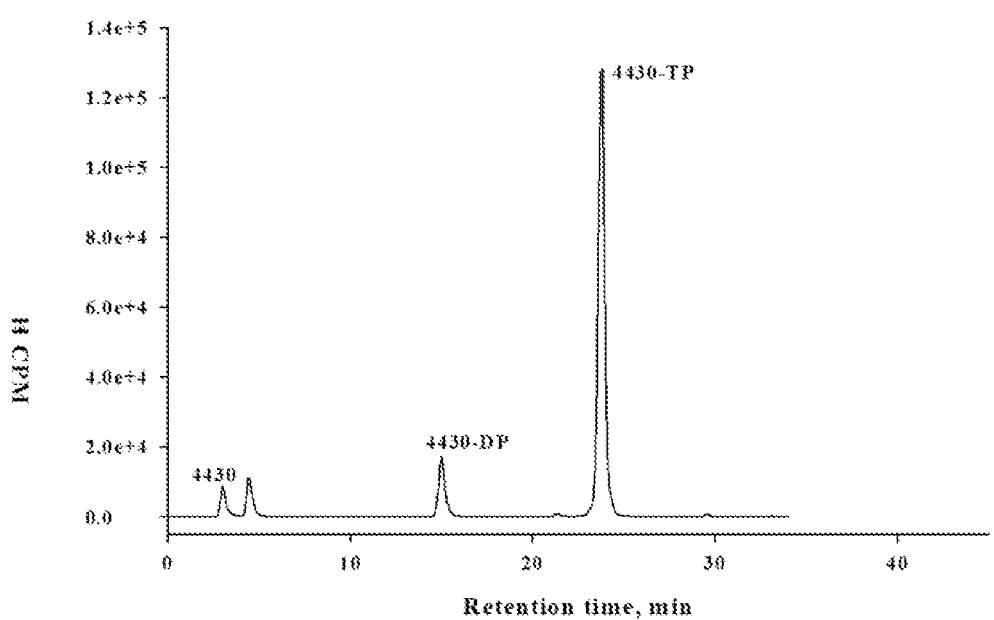
FIG. 1 shows the phosphorylation of compound 1 in human hepatocellular carcinoma (Huh-7) cells.

The invention provides compounds of formula I, or pharmaceutically acceptable salts thereof. The invention also provides methods and compositions for inhibition of viral nucleic acid polymerases, such as RNA and DNA polymerases, and methods and compositions that are useful for treating viral infections in subjects. The methods comprise administering to the subject an effective amount of: a compound of formula I, or a pharmaceutically acceptable salt thereof or a composition comprising a compound of formula I, or a pharmaceutically acceptable salt thereof, and a pharmaceutically acceptable carrier. The composition or method may optionally comprise one or more additional anti-viral agents.

In particular, the present invention relates to compounds of formula I, or pharmaceutically acceptable salts thereof and methods of treatment, suppression or and/or prevention of diseases or conditions relating to viral infection comprising administration of a compound of formula I, or pharmaceutically acceptable salt thereof.

In one aspect, the present invention is directed to a compound of formula I

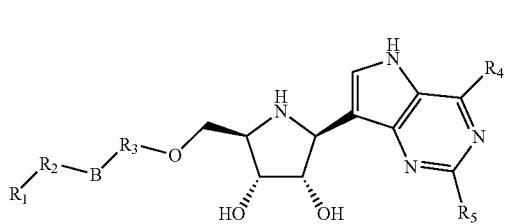

(I)

wherein $R_1$ is selected from

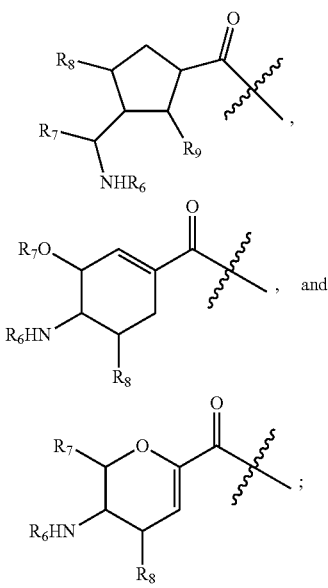

$R_2$ is a bond, O, or S;
$R_3$ is a bond, C(=O), C(=S), C(=NR$_{10}$), OC(=O), OC(=S), OC(=NR$_{10}$), N(R$_{11}$)C(=O), N(R$_{11}$)C(=S), or N(R$_{11}$)C(=NR$_{10}$);
$R_4$ is OH, or N(R$_{15}$)$_2$;
$R_5$ is H or N(R$_{15}$)$_2$;
$R_6$ is $R_{11}$, C(=O)—$R_{11}$, or SO$_2$—$R_{11}$;
$R_7$ is H or $R_{12}$, wherein $R_{12}$ is optionally substituted with one or more groups selected from lower alkyl, OR$_{11}$, O—C(=O)—R$_{11}$, O—C(=O)O—R$_{11}$, O—C(=O)N(R$_{11}$)$_2$, O—C(=S)—R$_{11}$, O—C(=S)O—R$_{11}$, and O—C(=S)N(R$_{11}$)$_2$;
$R_8$ is OR$_{11}$, O—C(=O)—R$_{11}$, O—C(=O)O—R$_{11}$, O—C(=O)N(R$_{11}$)$_2$, O—C(=S)—R$_{11}$, O—C(=S)O—R$_{11}$, O—C(=S)N(R$_{11}$)$_2$, N(R$_{11}$)$_2$, N(R$_{11}$)C(=O)—R$_{11}$, N(R$_{11}$)C(=O)O(R$_{11}$)$_2$, N(R$_{11}$)C(=O)N(R$_{11}$)$_2$, N(R$_{11}$)C(=S)—R$_{11}$, N(R$_{11}$)C(=S)O—R$_{11}$, N(R$_{11}$)C(=S)N(R$_{11}$)$_2$, or N(R$_{11}$)C(=NR$_{10}$)N(R$_{11}$)$_2$;

$R_9$ is H, OH, O—C(=O)O—R$_{11}$, O—C(=O)N(R$_{11}$)$_2$, O—C(=S)—R$_{11}$, O—C(=S)O—R$_{11}$, O—C(=S)N(R$_{11}$)$_2$;
B is a bond, $R_{12}$, $R_{12}$—$R_{13}$, $R_{12}$—$R_{13}$—$R_{14}$, $R_{12}$—O—$R_{13}$, $R_{12}$—S—$R_{13}$, $R_{12}$—N(R$_{11}$)$_2$—$R_{13}$, $R_{12}$—C(=O)—$R_{13}$, $R_{12}$—C(=S)—$R_{13}$, $R_{12}$—C(=NR$_{10}$)—$R_{13}$, $R_{12}$—OC(=O)—$R_{13}$, $R_{12}$—OC(=S)—$R_{13}$, $R_{12}$—OC(=NR$_{10}$)—$R_{13}$, $R_{12}$—SC(=O)—$R_{13}$, $R_{12}$—SC(=S)—$R_{13}$, $R_{12}$—SC(=NR$_{10}$)—$R_{13}$, $R_{12}$—N(R$_{11}$)C(=O)—$R_{13}$, $R_{12}$—N(R$_{11}$)C(=S)—$R_{13}$, $R_{12}$—N(R$_{11}$)C(=NR$_{10}$)—$R_{13}$, $R_{12}$—OC(=O)—OR$_{13}$, $R_{12}$—OC(=S)—OR$_{13}$, $R_{12}$—OC(=NR$_{10}$)—OR$_{13}$, $R_{12}$—OC(=O)—N(R$_{11}$)R$_{13}$, $R_{12}$—OC(=S)—N(R$_{11}$)R$_{13}$, $R_{12}$—OC(=NR$_{10}$)—N(R$_{11}$)R$_{13}$, $R_{12}$—OC(=O)—SR$_{13}$, $R_{12}$—OC(=S)—SR$_{13}$, $R_{12}$—OC(=NR$_{10}$)—SR$_{13}$, $R_{12}$—N(R$_{11}$)C(=O)—OR$_{13}$, $R_{12}$—N(R$_{11}$)C(=S)—OR$_{13}$, $R_{12}$—N(R$_{11}$)C(=NR$_{10}$)—OR$_{13}$, $R_{12}$—N(R$_{11}$)C(=O)—N(R$_{11}$)R$_{13}$, $R_{12}$—N(R$_{11}$)C(=S)—N(R$_{11}$)R$_{13}$, $R_{12}$—N(R$_{11}$)C(=NR$_{10}$)—N(R$_{11}$)R$_{13}$, $R_{12}$—N(R$_{11}$)C(=O)—SR$_{13}$, $R_{12}$—N(R$_{11}$)C(=S)—SR$_{13}$, $R_{12}$—N(R$_{11}$)C(=NR$_{10}$)—SR$_{13}$, $R_{12}$—SC(=O)—OR$_{13}$, $R_{12}$—SC(=S)—OR$_{13}$, $R_{12}$—SC(=NR$_{10}$)—OR$_{13}$, $R_{12}$—SC(=O)—SR$_{13}$, $R_{12}$—SC(=S)—SR$_{13}$, $R_{12}$—SC(=NR$_{10}$)—SR$_{13}$, $R_{12}$—SC(=O)—N(R$_{11}$)R$_{13}$, $R_{12}$—SC(=S)—N(R$_{11}$)R$_{13}$, or $R_{12}$—SC(=NR$_{10}$)—N(R$_{11}$)R$_{13}$; wherein each $R_{12}$, $R_{13}$, and $R_{14}$ are optionally substituted with one or more $R_{15}$;

$R_{10}$ is independently H, lower alkyl, lower alkenyl, lower alkynyl, lower cycloalkyl, aryl, heteroaryl, OR$_{11}$, or N(R$_{11}$)$_2$;

$R_{11}$ is independently H, lower alkyl, lower alkenyl, lower alkynyl, lower cycloalkyl, aryl, or heteroaryl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently halogen, $R_{10}$, OC(=O)R$_{11}$, OC(=S)R$_{11}$, OC(=NR$_{10}$)R$_{11}$, OC(=O)OR$_{11}$, OC(=S)OR$_{11}$, OC(=NR$_{10}$)OR$_{11}$, OC(=O)N(R$_{11}$)$_2$, OC(=S)N(R$_{11}$)$_2$, OC(=NR$_{10}$)N(R$_{11}$)$_2$, N(R$_{11}$)C(=O)R$_{11}$, N(R$_{11}$)C(=S)R$_{11}$, N(R$_{11}$)C(=NR$_{10}$)R$_{11}$, N(R$_{11}$)C(=O)OR$_{11}$, N(R$_{11}$)C(=S)OR$_{11}$, N(R$_{11}$)C(=NR$_{10}$)OR$_{11}$, N(R$_{11}$)C(=O)N(R$_{11}$)$_2$, N(R$_{11}$)C(=S)N(R$_{11}$)$_2$, or N(R$_{11}$)C(=NR$_{10}$)N(R$_{11}$)$_2$;

or a pharmaceutically acceptable salt thereof.

In certain embodiments, the compound of formula (I) is:

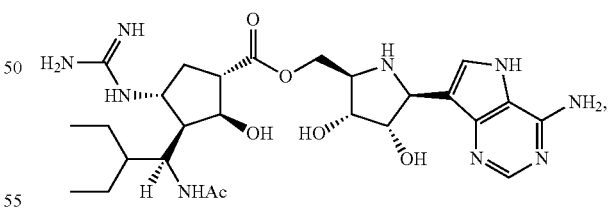

or a pharmaceutically acceptable salt thereof.

Abbreviations and Definitions

The abbreviation "PNP" refers to purine nucleoside phosphorylase.

The term "compound(s) of the invention" as used herein means a compound of formula I, and salts and tautomeric forms thereof.

The term "solvate" as used herein means a compound of formula I, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

A "pharmaceutical composition" refers to a mixture of one or more of the compounds described herein, or pharmaceutically acceptable salts, hydrates or pro-drugs thereof, with other chemical components, such as physiologically acceptable carriers and excipients. The purpose of a pharmaceutical composition is to facilitate administration of a compound to an organism.

The term "pharmaceutically acceptable salt" is intended to include salts derived from inorganic or organic acids or bases, including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; or salts with metals such as sodium, potassium, lithium, calcium, magnesium, and aluminum.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tartaric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically acceptable inorganic or organic bases. Inorganic bases include mineral bases such as halides, such as bromide and chloride, sulfates, phosphates and nitrates. Organic bases include all pharmaceutically acceptable aliphatic, alicyclic and aromatic amines and dibasic amino acids, examples of which include triethylamine and the like.

The term "lower alkyl" contemplates a straight or branched chain saturated hydrocarbon group containing 1-8 carbon atoms. Examples of $C_1$-$C_8$ straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

The term "lower alkenyl" contemplates a straight or branched chain non-cyclic hydrocarbon having from 2 to 8 carbon atoms and including at least one carbon-carbon double bond. Representative straight chain and branched $C_2$-$C_8$ alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, and the like.

The term "lower alkynyl" contemplates a straight or branched chain non-cyclic hydrocarbon having from 2 to 8 carbon atoms and including at least one carbon-carbon triple bond. Representative straight chain and branched $C_2$-$C_8$ alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, and the like.

The term "lower cycloalkyl" contemplates a monocyclic or bicyclic saturated ring consisting of carbon and hydrogen atoms and having 3-7 carbon atoms. Examples of lower cycloalkyl include, but are not limited to, cyclopropyl, cyclobutyl, cyclopentyl, cyclohexyl, cycloheptyl, and the like.

The term "aryl" contemplates a carbocyclic aromatic group. All of the ring atoms of an aryl group are carbon atoms. Aryl groups include compounds having one or more ring structures such as mono-, bi-, or tricyclic compounds as well as benzo-fused carbocyclic moieties such as 5,6,7,8-tetrahydronaphthyl and the like. In one embodiment, the aryl group is a monocyclic ring or bicyclic ring. Representative aryl groups include phenyl, tolyl, anthryl, fluorenyl, indenyl, azulenyl, phenanthryl and naphthyl. A carbocyclic aryl group may be unsubstituted or substituted.

The term "heteroaryl" contemplates an aromatic group comprised of at least one non-carbon atom in the aromatic ring. Representative heteroaryl groups include furanyl, thiophenyl, imidazolyl, oxazolyl, isoxazolyl, thiazolyl, triazolyl, tetrazolyl, pyrazolyl, pyridinyl, quinolinyl, isoquinolinyl, pyrazinyl, pyridazinyl, pyrimidinyl, benzimidazolyl, benzothiophenyl, or benzofuranyl, and the like. A heteroaryl group may be unsubstituted or substituted.

The term "amino acid" contemplates an organic compound containing an amine and an acid. Amino acids may be the "natural" amino acids as encoded by DNA, and may also be "unnatural" amino acids that are not encoded by DNA, including unnatural isomeric forms of natural amino acids. Amino acids encoded by DNA are well known in the art, and include, for example, glycine, serine, alanine, proline, aspartic acid, glutamic acid, arginine, asparagine, glutamine, tyrosine and the like. Unnatural amino acids include, for example, any natural amino acid that is further substituted with another functional group, or containing at least one additional carbon atom between the amine and acid functionalities (i.e., β-amino acids). Examples of unnatural amino acids include, for example, N-alkyl derivatives such as sarcosine, N-methyl phenylalanine and the like, β-alanine, and the like.

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of the viral infection, or one or more symptoms thereof, prevent the advancement of the viral infection, prevent the recurrence, development, or onset of one or more symptoms associated with the viral infection, prevent or reduce the replication or multiplication of a virus, prevent or reduce the production and/or release of a viral particle, enhance or otherwise improve the prophylactic or therapeutic effect(s) of another therapy. An effective amount also includes the amount of the compound of formula I that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin.

The terms "animal", "subject", and "patient" as used herein include all members of the animal kingdom including, but not limited to, birds, mammals, animals (e.g., cats, dogs, horses, and swine) and humans.

The terms "compound 1" and "BCX4430" are used interchangeably to refer to the following compound:

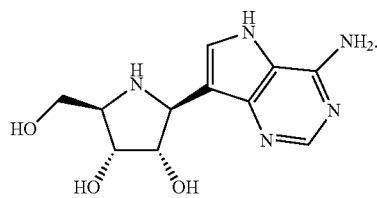 [SMILES: Nc1ncnc2c([C@@H]3N[C@H](CO)[C@@H](O)[C@H]3O)c[nH]c12]

Description

In particular, the present invention relates to a compound of formula I, and methods of treatment, suppression or and/or prevention of diseases or conditions relating to viral infection comprising administration to a subject in need thereof of an effective amount of a compound of formula I, or pharmaceutically acceptable salt thereof.

In one aspect, the present invention is directed to a compound of formula I:

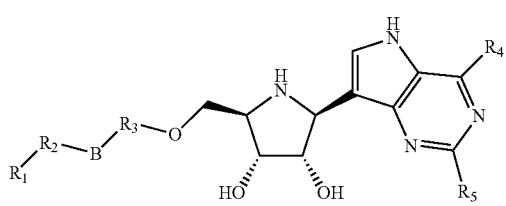

(I)

wherein $R_1$ is selected from

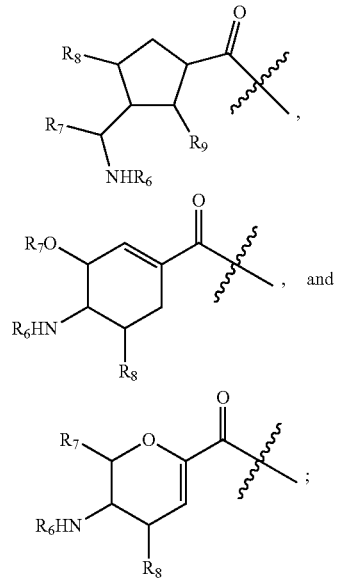

$R_2$ is a bond, O, or S;
$R_3$ is a bond, C(=O), C(=S), C(=NR$_{10}$), OC(=O), OC(=S), OC(=NR$_{10}$), N(R$_{11}$)C(=O), N(R$_{11}$)C(=S), or N(R$_{11}$)C(=NR$_{10}$);
$R_4$ is OH or N(R$_{15}$)$_2$;
$R_5$ is H or N(R$_{15}$)$_2$;
$R_6$ is $R_{11}$, C(=O)—R$_{11}$, or SO$_2$—R$_{11}$;
$R_7$ is H or $R_{12}$, wherein $R_{12}$ is optionally substituted with one or more groups selected from lower alkyl, OR$_{11}$, O—C(=O)—R$_{11}$, O—C(=O)O—R$_{11}$, O—C(=O)N(R$_{11}$)$_2$, O—C(=S)—R$_{11}$, O—C(=S)O—R$_{11}$, and O—C(=S)N(R$_{11}$)$_2$;
$R_8$ is OR$_{11}$, O—C(=O)—R$_{11}$, O—C(=O)O—R$_{11}$, O—C(=O)N(R$_{11}$)$_2$, O—C(=S)—R$_{11}$, O—C(=S)O—R$_{11}$, O—C(=S)N(R$_{11}$)$_2$, N(R$_{11}$)$_2$, N(R$_{11}$)C(=O)—R$_{11}$, N(R$_{11}$)C(=O)O(R$_{11}$)$_2$, N(R$_{11}$)C(=O)N(R$_{11}$)$_2$, N(R$_{11}$)C(=S)—R$_{11}$, N(R$_{11}$)C(=S)O—R$_{11}$, N(R$_{11}$)C(=S)N(R$_{11}$)$_2$, or N(R$_{11}$)C(=NR$_{10}$)N(R$_{11}$)$_2$;
$R_9$ is H, OH, O—C(=O)O—R$_{11}$, O—C(=O)N(R$_{11}$)$_2$, O—C(=S)—R$_{11}$, O—C(=S)O—R$_{11}$, O—C(=S)N(R$_{11}$)$_2$;
B is a bond, $R_{12}$, $R_{12}$—R$_{13}$, $R_{12}$—R$_{13}$—R$_{14}$, $R_{12}$—O—R$_{13}$, $R_{12}$—S—R$_{13}$, $R_{12}$—N(R$_{11}$)$_2$—R$_{13}$, $R_{12}$—C(=O)—R$_{13}$, $R_{12}$—C(=S)—R$_{13}$, $R_{12}$—C(=NR$_{10}$)—R$_{13}$, $R_{12}$—OC(=O)—R$_{13}$, $R_{12}$—OC(=S)—R$_{13}$, $R_{12}$—OC(=NR$_{10}$)—R$_{13}$, $R_{12}$—SC(=O)—R$_{13}$, $R_{12}$—SC(=S)—R$_{13}$, $R_{12}$—SC(=NR$_{10}$)—R$_{13}$, $R_{12}$—N(R$_{11}$)C(=O)—R$_{13}$, $R_{12}$—N(R$_{11}$)C(=S)—R$_{13}$, $R_{12}$—N(R$_{11}$)C(=NR$_{10}$)—R$_{13}$, $R_{12}$—OC(=O)—OR$_{13}$, $R_{12}$—OC(=S)—OR$_{13}$, $R_{12}$—OC(=NR$_{10}$)—OR$_{13}$, $R_{12}$—OC(=O)—N(R$_{11}$)R$_{13}$, $R_{12}$—OC(=S)—N(R$_{11}$)R$_{13}$, $R_{12}$—OC(=NR$_{10}$)—N(R$_{11}$)R$_{13}$, $R_{12}$—OC(=O)—SR$_{13}$, $R_{12}$—OC(=S)—SR$_{13}$, $R_{12}$—OC(=NR$_{10}$)—SR$_{13}$, $R_{12}$—N(R$_{11}$)C(=O)—OR$_{13}$, $R_{12}$—N(R$_{11}$)C(=S)—OR$_{13}$, $R_{12}$—N(R$_{11}$)C(=NR$_{10}$)—OR$_{13}$, $R_{12}$—N(R$_{11}$)C(=O)—N(R$_{11}$)R$_{13}$, $R_{12}$—N(R$_{11}$)C(=S)—N(R$_{11}$)R$_{13}$, $R_{12}$—N(R$_{11}$)C(=NR$_{10}$)—N(R$_{11}$)R$_{13}$, $R_{12}$—N(R$_{11}$)C(=O)—SR$_{13}$, $R_{12}$—N(R$_{11}$)C(=S)—SR$_{13}$, $R_{12}$—N(R$_{11}$)C(=NR$_{10}$)—SR$_{13}$, $R_{12}$—SC(=O)—OR$_{13}$, $R_{12}$—SC(=S)—OR$_{13}$, $R_{12}$—SC(=NR$_{10}$)—OR$_{13}$, $R_{12}$—SC(=O)—SR$_{13}$, $R_{12}$—SC(=S)—SR$_{13}$, $R_{12}$—SC(=NR$_{10}$)—SR$_{13}$, $R_{12}$—SC(=O)—N(R$_{11}$)OR$_{13}$, $R_{12}$—SC(=S)—N(R$_{11}$)R$_{13}$, or $R_{12}$—SC(=NR$_{10}$)—N(R$_{11}$)R$_{13}$; wherein each $R_{12}$, $R_{13}$, and $R_{14}$ are optionally substituted with one or more $R_{15}$;

$R_{10}$ is independently H, lower alkyl, lower alkenyl, lower alkynyl, lower cycloalkyl, aryl, heteroaryl, $OR_{11}$, or $N(R_{11})_2$;

$R_{11}$ is independently H, lower alkyl, lower alkenyl, lower alkynyl, lower cycloalkyl, aryl, or heteroaryl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently halogen, $R_{10}$, $OC(=O)R_{11}$, $OC(=S)R_{11}$, $OC(=NR_{10})R_{11}$, $OC(=O)OR_{11}$, $OC(=S)OR_{11}$, $OC(=NR_{10})OR_{11}$, $OC(=O)N(R_{11})_2$, $OC(=S)N(R_{11})_2$, $OC(=NR_{10})N(R_{11})_2$, $N(R_{11})C(=O)R_{11}$, $N(R_{11})C(=S)R_{11}$, $N(R_{11})C(=NR_{10})R_{11}$, $N(R_{11})C(=O)OR_{11}$, $N(R_{11})C(=S)OR_{11}$, $N(R_{11})C(=NR_{10})OR_{11}$, $N(R_{11})C(=O)N(R_{11})_2$; $N(R_{11})C(=S)N(R_{11})_2$, or $N(R_{11})C(=NR_{10})N(R_{11})_2$;

or a pharmaceutically acceptable salt thereof.

In one embodiment of the compound of formula I, $R_1$ is selected from

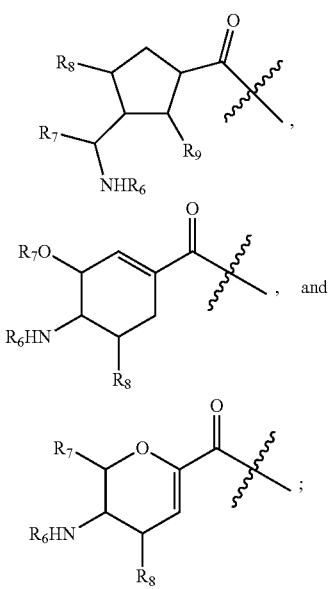

$R_2$ is a bond, O, or S;
$R_3$ is a bond, $C(=O)$, $C(=S)$, $C(=NR_{10})$, $OC(=O)$, $OC(=S)$, $OC(=NR_{10})$, $N(R_{11})C(=O)$, $N(R_{11})C(=S)$, or $N(R_{11})C(=NR_{10})$;
$R_4$ is OH or $N(R_{15})_2$;
$R_5$ is H or $N(R_{15})_2$;
$R_6$ is $R_{11}$, $C(=O)-R_{11}$, or $SO_2-R_{11}$;
$R_7$ is H or $R_{12}$, wherein $R_{12}$ is optionally substituted with one or more groups selected from lower alkyl, $OR_{11}$, $O-C(=O)-R_{11}$, $O-C(=O)O-R_{11}$, and $O-C(=O)N(R_{11})_2$;
$R_8$ is $OR_{11}$, $O-C(=O)-R_{11}$, $O-C(=O)O-R_{11}$, $O-C(=O)N(R_{11})_2$, $O-C(=S)-R_{11}$, $O-C(=S)O-R_{11}$, $O-C(=S)N(R_{11})_2$, $N(R_{11})_2$, $N(R_{11})C(=O)-R_{11}$, $N(R_{11})C(=O)O(R_{11})_2$, $N(R_{11})C(=S)-R_{11}$, $N(R_{11})C(=S)O-R_{11}$, or $N(R_{11})C(=NR_{10})N(R_{11})_2$;
$R_9$ is H, OH, $O-C(=O)-R_{11}$, $O-C(=O)N(R_{11})_2$, $O-C(=S)-R_{11}$, $O-C(=S)O-R_{11}$, $O-C(=S)N(R_{11})_2$;
B is a bond, $R_{12}$, $R_{12}-R_{13}$, $R_{12}-R_{13}-R_{14}$, $R_{12}-O-R_{13}$, $R_{12}-OC(=O)-R_{13}$, $R_{12}-N(R_{11})C(=O)-R_{13}$, $R_{12}-OC(=O)-OR_{13}$, $R_{12}-OC(=O)-N(R_{11})R_{13}$, $R_{12}-N(R_{11})C(=O)-OR_{13}$, or $R_{12}-N(R_{11})C(=O)-N(R_{11})R_{13}$; wherein each $R_{12}$, $R_{13}$, and $R_{14}$ are optionally substituted with one or more $R_{15}$;

$R_{10}$ is independently H, lower alkyl, lower alkenyl, lower alkynyl, lower cycloalkyl, aryl, heteroaryl, $OR_{11}$, or $N(R_{11})_2$;

$R_{11}$ is independently H, or lower alkyl optionally substituted with one or more lower alkyl, lower alkenyl, lower alkynyl, aryl or heteroaryl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently halogen, $R_{10}$, $OC(=O)R_{11}$, $OC(=S)R_{11}$, $OC(=NR_{10})R_{11}$, $OC(=O)OR_{11}$, $OC(=S)OR_{11}$, $OC(=NR_{10})OR_{11}$, $OC(=O)N(R_{11})_2$, $OC(=S)N(R_{11})_2$, $OC(=NR_{10})N(R_{11})_2$, $N(R_{11})C(=O)R_{11}$, $N(R_{11})C(=S)R_{11}$, $N(R_{11})C(=NR_{10})R_{11}$, $N(R_{11})C(=O)OR_{11}$, $N(R_{11})C(=S)OR_{11}$, $N(R_{11})C(=NR_{10})OR_{11}$, $N(R_{11})C(=O)N(R_{11})_2$, $N(R_{11})C(=S)N(R_{11})_2$, or $N(R_{11})C(=NR_{10})N(R_{11})_2$;

or a pharmaceutically acceptable salt thereof.

In another embodiment of the compound of formula I, $R_1$ is selected from

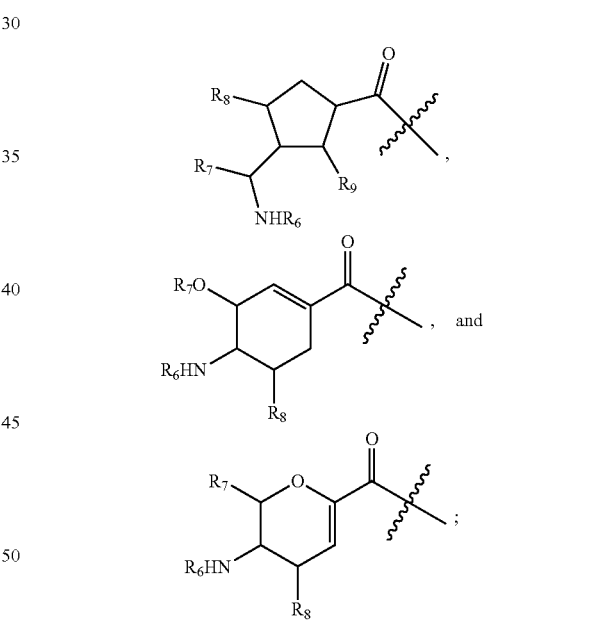

$R_2$ is a bond, O, or S;
$R_3$ is a bond, $C(=O)$, $C(=S)$, or $N(R_{11})C(=O)$;
$R_4$ is OH or $NH_2$;
$R_5$ is H or $NH_2$;
$R_6$ is $C(=O)-R_{11}$, or $SO_2-R_{11}$;
$R_7$ is lower alkyl, optionally substituted with one or more groups selected from lower alkyl, $OR_{11}$, $O-C(=O)-R_{11}$, $O-C(=O)O-R_{11}$, and $O-C(=O)N(R_{11})_2$;
$R_8$ is $OR_{11}$, $O-C(=O)-R_{11}$, $O-C(=O)O-R_{11}$, $O-C(=O)N(R_{11})_2$, $O-C(=S)-R_{11}$, $O-C(=S)N(R_{11})_2$, $N(R_{11})_2$, $N(R_{11})C(=O)O(R_{11})_2$, or $N(R_{11})C(=NR_{10})N(R_{11})_2$;
$R_9$ is H, OH, $O-C(=O)O-R_{11}$, or $O-C(=O)N(R_{11})_2$;

B is a bond, $R_{12}$, $R_{12}$—$R_{13}$, $R_{12}$—O—$R_{13}$, $R_{12}$—OC(=O)—$R_{13}$, $R_{12}$—N($R_{11}$)C(=O)—$R_{13}$, $R_{12}$—OC(=O)—O$R_{13}$, $R_{12}$—OC(=O)—N($R_{11}$)$R_{13}$, $R_{12}$—N($R_{11}$)C(=O)—O$R_{13}$, or $R_{12}$—N($R_{11}$)C(=O)—N($R_{11}$)$R_{13}$; wherein each $R_{12}$, $R_{13}$, and $R_{14}$ are optionally substituted with one or more $R_{15}$;

$R_{10}$ is independently H, lower alkyl, lower alkenyl, lower alkynyl, lower cycloalkyl, aryl, heteroaryl, O$R_{11}$, or N($R_{11}$)$_2$;

$R_{11}$ is independently H, or lower alkyl optionally substituted with one or more lower alkyl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently $R_{10}$, N($R_{11}$)C(=O)$R_{11}$, or N($R_{11}$)C(=O)O$R_{11}$;

or a pharmaceutically acceptable salt thereof.

In still another embodiment of the compound of formula I, $R_1$ is selected from

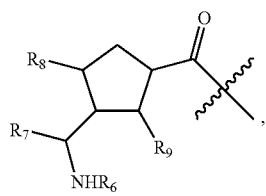

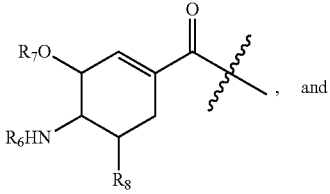

, and

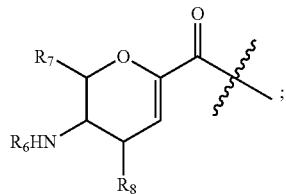

;

$R_2$ is a bond, O, or S;
$R_3$ is a bond, C(=O), C(=S), or N($R_{11}$)C(=O);
$R_4$ is OH or NH$_2$;
$R_5$ is H or NH$_2$;
$R_6$ is C(=O)—$R_{11}$;
$R_7$ is lower alkyl, optionally substituted with one or more groups selected from lower alkyl, O$R_{11}$, O—C(=O)—$R_{11}$, O—C(=O)O—$R_{11}$, and O—C(=O)N($R_{11}$)$_2$;
$R_8$ is O$R_{11}$, O—C(=O)—$R_{11}$, O—C(=O)O—$R_{11}$, O—C(=O)N($R_{11}$)$_2$, N($R_{11}$)$_2$, N(H)C(=O)O($R_{11}$)$_2$, or N(H)C(=NH)NH$_2$;
$R_9$ is H, OH, O—C(=O)O—$R_{11}$, or O—C(=O)N($R_{11}$)$_2$;
B is a bond, $R_{12}$, $R_{12}$—$R_{13}$, $R_{12}$—O—$R_{13}$, $R_{12}$—OC(=O)—$R_{13}$, $R_{12}$—N($R_{11}$)C(=O)—$R_{13}$, $R_{12}$—OC(=O)—O$R_{13}$, $R_{12}$—OC(=O)—N($R_{11}$)$R_{13}$, $R_{12}$—N($R_{11}$)C(=O)—O$R_{13}$, or $R_{12}$—N($R_{11}$)C(=O)—N($R_{11}$)$R_{13}$; wherein each $R_{12}$, $R_{13}$, and $R_{14}$ are optionally substituted with one or more $R_{15}$;

$R_{10}$ is independently H, lower alkyl, lower alkenyl, lower alkynyl, lower cycloalkyl, aryl, heteroaryl, O$R_{11}$, or N($R_{11}$)$_2$;

$R_{11}$ is independently H, or lower alkyl optionally substituted with one or more lower alkyl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently $R_{10}$, N($R_{11}$)C(=O)$R_{11}$, or N($R_{11}$)C(=O)O$R_{11}$;

or a pharmaceutically acceptable salt thereof.

In yet another embodiment of the compound of formula I, $R_1$ is

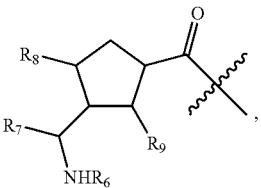

In yet another embodiment of the compound of formula I, $R_1$ is

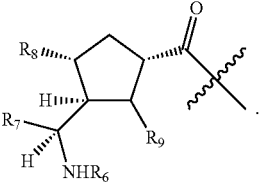

.

In yet another embodiment of the compound of formula I, $R_1$ is

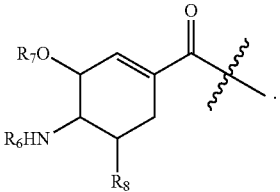

.

In yet another embodiment of the compound of formula I, $R_1$ is

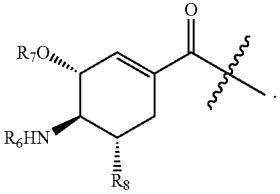

.

In yet another embodiment of the compound of formula I, $R_1$ is

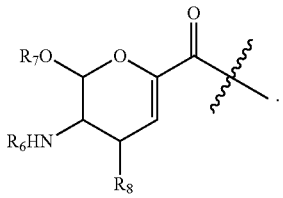

In yet another embodiment of the compound of formula I, $R_1$ is

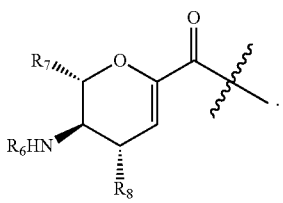

In another embodiment of the compound of formula I, $R_1$ is

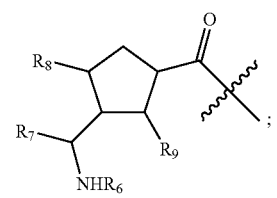

$R_2$ is a bond, or O;
$R_3$ is a bond or C(=O);
$R_4$ is $NH_2$;
$R_5$ is hydrogen;
$R_6$ is C(=O)—$CH_3$;
$R_7$ is —CH($CH_2CH_3$)$_2$;
$R_8$ is N(H)C(=NH)$NH_2$;
$R_9$ is OH;
B is a bond, lower alkyl, lower alkyl-OC(=O)—$R_{13}$; wherein $R_{13}$ is optionally substituted with $R_{15}$;
$R_{11}$ is independently H, or lower alkyl;
$R_{13}$ is lower alkyl; and
$R_{15}$ is lower alkyl, N($R_{11}$)$_2$, or N(H)C(=O)$R_{11}$;
or a pharmaceutically acceptable salt thereof.

In another embodiment of the compound of formula I, $R_1$ is

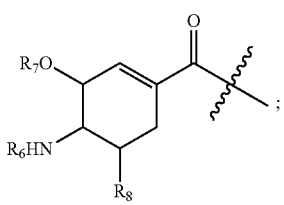

$R_2$ is a bond or O;
$R_3$ is a bond or C(=O);
$R_4$ is $NH_2$;
$R_5$ is hydrogen;
$R_6$ is C(=O)—$CH_3$;
$R_7$ is —CH($CH_2CH_3$)$_2$;
$R_8$ is $NH_2$;
B is a bond, lower alkyl, lower alkyl-OC(=O)—$R_{13}$; wherein $R_{13}$ is optionally substituted with $R_{15}$;
$R_{11}$ is independently H, or lower alkyl;
$R_{13}$ is lower alkyl; and
$R_{15}$ is lower alkyl, N($R_{11}$)$_2$, or N(H)C(=O)$R_{11}$;
or a pharmaceutically acceptable salt thereof.

In still another embodiment of the compound of formula I, $R_1$ is

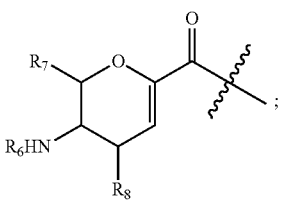

$R_2$ is a bond or O;
$R_3$ is a bond or C(=O);
$R_4$ is $NH_2$;
$R_5$ is hydrogen;
$R_6$ is C(=O)—$CH_3$;
$R_7$ is 1,2,3-trihydroxypropyl;
$R_8$ is $NH_2$C(=NH)$NH_2$;
B is a bond, lower alkyl, lower alkyl-OC(=O)—$R_{13}$; wherein $R_{13}$ is optionally substituted with $R_{15}$;
$R_{11}$ is independently H, or lower alkyl;
$R_{13}$ is lower alkyl; and
$R_{15}$ is lower alkyl, N($R_{11}$)$_2$, or N(H)C(=O)$R_{11}$;
or a pharmaceutically acceptable salt thereof.

The compounds of the invention are comprised of a neuraminidase inhibitor scaffold joined via a chemical linker to a nucleic acid polymerase inhibitor scaffold. Thus, the compounds of the invention are comprised of two anti-viral compounds embodied in the compound of formula I. In one embodiment, the compound of formula I is a pro-drug. When administered to a subject, the linker may be cleaved to release the neuraminidase inhibitor and the polymerase inhibitor. The neuraminidase inhibitor and the polymerase inhibitor operate via different mechanisms of action. Treatment of a viral infection, such as HIV, with more than one anti-viral compound has been proven to inhibit the development of viral resistance. Thus, the compounds of formula I may improve resistance and efficacy relative to methods comprising individual administration of a neuraminidase inhibitor or a polymerase inhibitor.

In one embodiment, a neuraminidase inhibitor may be generated from the compound of formula I following administration to a subject.

In one embodiment, a polymerase inhibitor may be generated from the compound of formula I following administration to a subject.

In one embodiment, a neuraminidase inhibitor and a polymerase inhibitor may both be generated from the compound of formula I following administration to a subject.

In one embodiment, the neuraminidase inhibitor is zanamivir. In another embodiment, the neuraminidase inhibitor is oseltamivir. In yet another embodiment, the neuraminidase inhibitor is peramivir.

In one embodiment, the polymerase inhibitor is compound A:

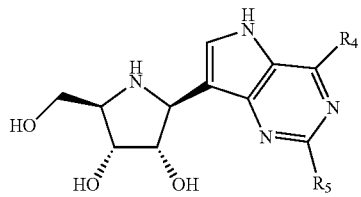

Compound A wherein $R_4$ is OH or $N(R_{15})_2$; and $R_5$ is H or $N(R_{15})_2$.

In one embodiment, compound A is generated in vivo from a compound of formula I.

In one embodiment, $R_4$ is OH or $N(R_{15})_2$; and $R_5$ is H or $N(R_{15})_2$.

In another embodiment, $R_4$ is $N(R_{15})_2$. In another embodiment, $R_4$ is $NH_2$. In yet another embodiment, $R_4$ is OH.

In another embodiment, $R_5$ is hydrogen. In another embodiment, $R_5$ is $N(R_{15})_2$. In yet another embodiment, $R_5$ is $NH_2$.

In one embodiment, B is comprised of an amino acid radical or derivative thereof linked to $R_2$ and $R_3$. In another embodiment, the amino acid radical or derivative thereof is linked to $R_2$ via the side-chain of the amino acid radical. In still another embodiment, the amino acid radical or derivative thereof is linked to $R_3$ via the acyl group of the amino acid radical.

Specific embodiments of B include, but are not limited to,

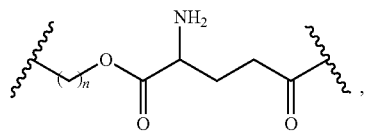

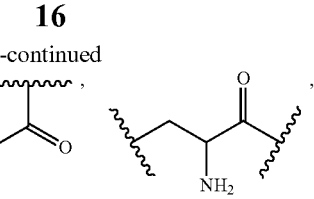

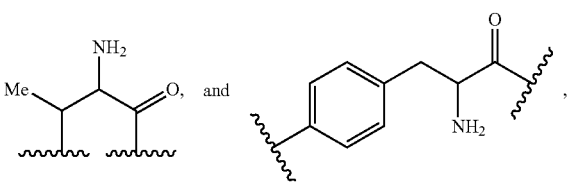

wherein n is an integer between 1 and 8.

Amino acid radicals need not be limited to radicals derived from amino acids encoded by DNA or naturally occurring amino acids, and may be of either D- or L-configuration.

In another specific embodiment, the compound of formula I is

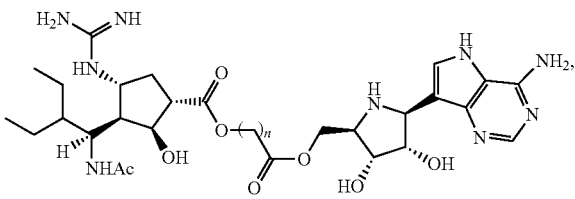

wherein n is an integer between 1 and 6.

In still another specific embodiment, the compound of formula I is

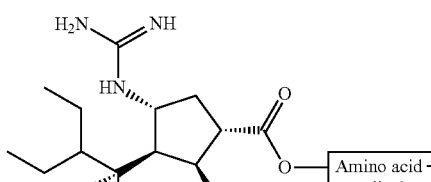 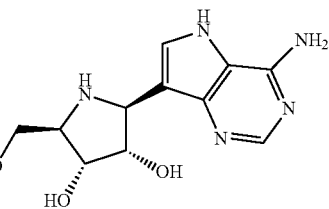

In still another specific embodiment, the compound of formula I is

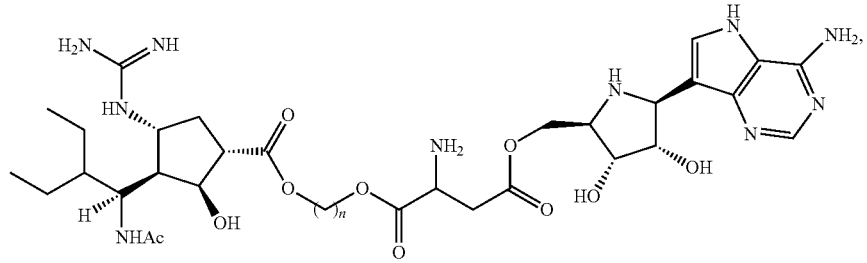

wherein n is an integer between 1 and 6.

In still another specific embodiment, the compound of formula I is

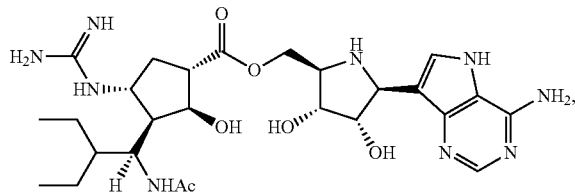 [SMILES: CCC(CC)[C@H](NC(C)=O)[C@@H]1[C@H](O)[C@@H](C(=O)OC[C@H]2N[C@@H](c3c[nH]c4c(N)ncnc34)[C@H](O)[C@@H]2O)C[C@H]1NC(=N)N]

or a pharmaceutically acceptable salt thereof.

The compounds of formula I exist in isomeric forms, such as, for example, stereoisomers such as enantiomers and diastereomers, as well as mixtures thereof; tautomeric forms, solvates and hydrates, all of which are embodied within the scope of the invention.

Thus, in one embodiment, the compound of formula I is a racemic mixture. In another embodiment, the compound of formula I is a mixture of one or more diastereomeric isomers. In yet another embodiment, the compound of formula I is enriched in one enantiomer. In still another embodiment, the compound of formula I is enriched in one diastereomer.

The compounds of the present invention are prepared in different forms, such as salts, hydrates, solvates, or complexes, and the invention includes compounds, compositions and methods encompassing all variant forms of the compounds.

In another embodiment, the present invention provides a method for treating a subject suffering from a viral infection comprising administering to said subject a compound of formula I, or pharmaceutically acceptable salt thereof.

In still another embodiment, the present invention provides a method for suppressing a viral infection in a subject comprising administering to the subject a compound of formula I, or pharmaceutically acceptable salt thereof.

In one embodiment, the method is performed in vitro. In another embodiment, the method is performed in vivo.

In one embodiment, the present invention provides a method for inhibiting a nucleic acid polymerase in a cell, comprising contacting said cell with a compound of formula I, or a pharmaceutically acceptable salt thereof. In one embodiment, the method is performed in vitro. In another embodiment, the method is performed in vivo. In one embodiment, the cell is in a bodily fluid. In one embodiment, the bodily fluid is blood. In another embodiment, the bodily fluid is plasma. In still another embodiment, the bodily fluid is blood serum.

In one embodiment, the present invention provides a method for inhibiting a neuraminidase in a cell, comprising contacting said cell with a compound of formula I, or a pharmaceutically acceptable salt thereof. In one embodiment, the method is performed in vitro. In another embodiment, the method is performed in vivo. In one embodiment, the cell is in a bodily fluid. In one embodiment, the bodily fluid is blood. In another embodiment, the bodily fluid is plasma. In still another embodiment, the bodily fluid is blood serum.

In another embodiment, the subject is a mammal. In yet another embodiment, the subject is a human. In yet another embodiment, the subject is avian. In still another embodiment, the subject is a swine or pig.

In another embodiment, the compound or composition is administered intravenously.

In another embodiment, the compound or composition is administered intramuscularly.

In another embodiment, the compound or composition is administered orally.

In one embodiment of the invention, the compounds of the invention are used to treat or prevent a viral infection associated with a virus. In another embodiment, the compounds of the invention are used to inhibit the replication or infectivity of a virus. In yet another embodiment, the compounds of the invention are used to inhibit the growth of a cell infected with a virus. Examples of said viruses include, but are not limited to, viruses of the orthmyxoviridae, paramyxoviridae, arenaviridae, bunyaviridae, flaviviridae, and coronaviridae families. Specific examples of viruses include, but are not limited to, influenza A and B, including subtypes thereof, Junin, Dengue Fever, yellow fever, measles, and SARS-CoV.

Thus, in one embodiment, the virus is selected from the group consisting of viruses of the orthmyxoviridae, paramyxoviridae, arenaviridae, bunyaviridae, flaviviridae, and coronaviridae families. In yet another embodiment, the viral infection comprises a virus selected from the group consisting of influenza A and B, including subtypes thereof, Junin, Dengue Fever, yellow fever, and measles. In still another embodiment, the viral infection is influenza A or B, or subtypes thereof.

In another embodiment, the present invention provides a method for inhibiting a viral RNA or DNA polymerase in a subject comprising administering to said subject a compound of formula I, or a pharmaceutically acceptable salt thereof.

In one embodiment, the RNA viral polymerase is selected from the group consisting of polymerases of the orthmyxoviridae, paramyxoviridae, arenaviridae, bunyaviridae, flaviviridae, and coronaviridae families. In yet another embodiment, the RNA viral polymerase comprises a polymerase selected from the group consisting of influenza A and B, including subtypes thereof, Junin, Dengue Fever, yellow fever, and measles polymerase. In still another embodiment, the RNA viral polymerase is influenza A or B, or subtypes thereof.

The composition or method may further comprise one or more additional anti-viral agents in combination with a compound of formula I. Examples of such anti-viral agents include, but are not limited to, Cytovene, Ganciclovir, trisodium phosphonoformate, ribavirin, interferon, d4T, ddI, AZT, and Amantadine, Rimandatine, and other anti-influenza agents; Acyclovir, and related agents, Foscarnet and other anti-herpes virus agents. Non-limiting examples of neuraminidase inhibitors include laninamivir, oseltamivir, zanamivir, and peramivir.

Compounds that relate to inhibition of influenza polymerase are described, for example, in U.S. Pat. Nos. 7,388, 002; 7,560,434; and in U.S. patent application Ser. Nos. 12/440,697; and 12/398,866; all of which are hereby incorporated by reference. Currently, there is at least one influenza polymerase inhibitor in clinical trials, known as T-705 (favipiravir; 6-fluoro-3-hydroxy-2-pyrazinecarboxamide). T-705 possesses potent and broad spectrum antiviral activity against multiple strains of influenza virus infection in vitro and in vivo (Kiso et al., *PNAS* 2010, 107, 882-887). T-705 is characterized by a mechanism of action that is different from most anti-influenza viral drugs.

Another class of compounds used as anti-virals are M2 inhibitors (see Pielak, R., Schnell, J., and Chou, J. *PNAS* 2009, 106(18), 7379-7384). Exemplary members of this class include amantadine and rimantadine.

Thus, in one embodiment, the aforementioned methods of the invention further comprise administration of one or more additional anti-viral agents.

In one embodiment, an additional anti-viral agent is selected from the group consisting of Cytovene, Ganciclovir, trisodium phosphonoformate, ribavirin, interferon, d4T, ddI, AZT, and amantadine, rimandatine, T-705 and other anti-influenza agents; Acyclovir, and related agents, Foscarnet and other anti-herpes virus agents.

In one embodiment, an additional anti-viral agent is an anti-influenza agent. In another embodiment, an additional anti-viral agent is a neuraminidase inhibitor. In another embodiment, an additional anti-viral agent is selected from the group consisting of laninamivir, oseltamivir, zanamivir, and peramivir. In yet another embodiment, an additional anti-viral agent is peramivir.

In one embodiment, an additional anti-viral agent is an M2 inhibitor. In another embodiment, an additional anti-viral agent is selected from the group consisting of amantadine and rimandatine.

In one embodiment, the methods of the invention comprise administration of two additional anti-viral agents. In another embodiment, the additional anti-viral agents are a neuraminidase inhibitor and an M2 inhibitor. In another embodiment, the additional anti-viral agents are selected from the groups consisting of 1) laninamivir, oseltamivir, zanamivir, and peramivir; and 2) amantadine and rimandatine. In still another embodiment, the additional antiviral agents are peramivir and amantadine. In yet another embodiment, the additional antiviral agents are peramivir and rimantadine.

The invention provides compounds, methods and compositions for inhibition of viral nucleic acid polymerases, such as RNA and DNA polymerases, and methods and compositions that are useful for treating viral infections in subjects. The methods comprise administering to the subject in need thereof an effective amount of a compound of formula I, or a pharmaceutically acceptable salt thereof; or a composition comprising a compound of formula I, or a pharmaceutically acceptable salt thereof, and a pharmaceutically acceptable carrier. The composition or method may optionally comprise one or more additional anti-viral agents.

In particular, the present invention relates to compounds of formula I, or a pharmaceutically acceptable salt thereof; and methods of treatment, suppression or and/or prevention of diseases or conditions relating to viral infection comprising administration of a compound of formula I, or pharmaceutically acceptable salt thereof.

The present invention provides methods and compositions for inhibition of viral nucleic acid polymerases, such as DNA and/or RNA viral polymerases, and methods and compositions that are useful for treating viral infections in subjects. The methods comprise administering to the subject an effective amount of a compound of formula I, or a pharmaceutically acceptable salt or pro-drug thereof, or a composition comprising a compound of formula I, or a pharmaceutically acceptable salt thereof, and a pharmaceutically acceptable carrier. The composition or method may optionally comprise one or more additional anti-viral agents.

The imino-ribitol components in the compounds of formula I are 9-deazaadenine derivatives generally known as immucillins, and are described, for example, in WO 03/80620, and by Evans et al. in *Tetrahedron* 2000, 56, 3053 and *J. Org. Chem.* 2001, 66(17), 5723. Syntheses of similar structures are discussed, for example, in U.S. Pat. Nos. 5,985,848; 6,066,722; 6,228,741 and PCT publications WO 2003/080620 and 2008/030119; all of which are hereby incorporated by reference. Immucillin derivatives have been studied as PNP inhibitors (see Kicska et al., *J. Biol. Chem.* 2002, 277, 3219-3225, and Kicska et al., *J. Biol. Chem.* 2002, 277, 3226-3231). Some immucillins have also been studied as 5'-methylthioadenosine phosphorylase (MTAP) or 5'-methylthioadenosine nucleosidase (MTAN) inhibitors. Such mechanisms have been implicated in the treatment of cancer and bacterial infections (see WO 03/080620; incorporated by reference).

The neuraminidase inhibitor components in the compounds of formula I are carbocyclic or heterocyclic derivatives generally embodied within $R_1$, and are described, for example, in U.S. Pat. Nos. 5,360,817; 5,648,379; 5,866,601; 5,952,375; 6,294,572; 6,495,711; 6,503,745; and 6,562,861; all of which are hereby incorporated by reference.

The compounds of formula I may exhibit tautomeric properties. Thus, the present invention also encompasses tautomeric forms of compounds of formula I, and mixtures thereof. It will further be appreciated that some compounds exist as pharmaceutically acceptable salts, solvates, and hydrates, each of which are also within the embodiments of the invention.

In another embodiment, the compound of formula I exists as a pharmaceutically acceptable salt.

The compounds of the disclosure therefore are useful in treating and/or preventing viral infections in a host or subject. The methods of the invention may be used in treating and/or preventing disease states or conditions caused by and/or related to such viral infections. Examples of such viral infections include, but are not limited to, hepatitis, immunodeficiency virus, polio, measles, Ebola, Coxsackie, Rhino, West Nile, small pox, encephalitis, yellow fever, Dengue fever, and influenza (including human, avian, and swine).

The present invention provides methods for inhibiting a viral RNA or DNA polymerase comprising contacting the polymerase with an effective inhibitory amount of the compound of formula I, or a pharmaceutically acceptable salt thereof.

In another embodiment, the present invention provides a method for treating a subject suffering from an RNA viral infection which comprises administering to said patient a effective amount of a compound of formula I, or pharmaceutically acceptable salt thereof.

In one embodiment, the disclosure provides for the use of pharmaceutical compositions and/or medicaments comprised of the compound of formula I in a method of treating a viral infection, and/or disease state, and/or condition caused by or related to such viral infection.

In one embodiment, the treatment results from the inhibition of a viral DNA or RNA polymerase.

In another embodiment, the method of treatment comprises the steps of: (i) identifying a subject in need of such treatment; (ii) providing a compound of formula I, or a pharmaceutically acceptable salt thereof, or a composition comprising a compound of formula I, or a pharmaceutically acceptable salt thereof; and (iii) administering said compound or composition in a therapeutically effective amount to treat the viral infection in the subject or to inhibit the activity of viral DNA or RNA polymerase in a subject in need of such treatment.

In one embodiment, the prevention or suppression of the viral infection or disease state results from the inhibition of a viral DNA or RNA polymerase.

The methods comprise administering to the subject an effective amount of a compound of formula I, or a pharmaceutically acceptable salt thereof, or a composition comprising a compound of formula I, or a pharmaceutically acceptable salt thereof, and a pharmaceutically acceptable carrier. The pharmaceutically acceptable carriers are well-known to those skilled in the art, and include, for example, adjuvants, diluents, excipients, fillers, lubricants and vehicles. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols.

In another embodiment, the method of prevention or suppression of the viral infection or disease state comprises the steps of: (i) identifying a subject in need of such treatment; (ii) providing a compound of formula I, or a pharmaceutically acceptable salt thereof, or a composition comprising a compound of formula I, or a pharmaceutically acceptable salt thereof; and (iii) administering said compound or composition in a therapeutically effective amount to prevent or suppress the viral infection or disease state in the subject or to inhibit the activity of viral DNA or RNA polymerase in a subject in need of such treatment.

The compounds of the present invention are prepared in different forms, such as salts, hydrates, solvates, or complexes, and the invention includes methods encompassing all variant forms of the compounds.

The compounds of the present invention encompass all geometric and optical isomers, including diastereomers and enantiomers thereof, as well as cis- and trans-isomers, and mixtures thereof such as, for example, racemates.

In another embodiment, the methods of the invention comprise pharmaceutically acceptable salts of the compound of formula I. A compound of formula I also can be formulated as a pharmaceutically acceptable salt, e.g., acid addition salts, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The subjects of the invention are in vitro and in vivo systems, including, for example, isolated or cultured cells or tissues, non-cellular in vitro assay systems and animals (e.g., an amphibian, a bird, a fish, a mammal, a marsupial, a human, a domestic animal such as, for example, a cat, dog, monkey, mouse or rat; or a commercial animal such as, for example, a cow or pig).

The compounds of the invention are formulated into pharmaceutical compositions for administration to subjects in a biologically compatible form suitable for administration in vivo. According to another aspect, the present invention provides a pharmaceutical composition comprising compounds of formula I in admixture with a pharmaceutically acceptable diluent and/or carrier. The pharmaceutically-acceptable carrier must be "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In one embodiment, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, When administered to a subject, the compounds of formula I and pharmaceutically acceptable carriers may be sterile. In one embodiment, water is a carrier when the compound of formula I is administered intravenously. Saline solutions and aqueous dextrose and glycerol solutions may also be employed as liquid carriers, particularly for injectable solutions. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. For example, the compounds of formula I are brought into association with a carrier and/or diluent, as a suspension or solution. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds of the present invention are administered to a human or animal subject by known procedures including, without limitation, oral administration, sublingual or buccal administration, parenteral administration, transdermal administration, via inhalation or intranasally, vaginally, rectally, and intramuscularly. The compounds of the invention are administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter. In one embodiment, the agent is administered to the subject by way of intramuscular delivery. In another embodiment, the agent is administered to the subject by way of intravenous delivery. In yet another embodiment, the agent is administered orally.

For oral administration, a formulation of the compounds of the invention may be presented as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation.

For parenteral administration (i.e., administration by injection through a route other than the alimentary canal), the compounds of the invention are combined with a sterile aqueous solution that is isotonic with the blood of the subject. Such a formulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation may be presented in unit or multi-dose containers, such as sealed ampules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's body.

Parenteral administration includes aqueous and non-aqueous based solutions. Examples of which include, for example, water, saline, aqueous sugar or sugar alcohol solutions, alcoholic (such as ethyl alcohol, isopropanol, glycols), ethers, oils, glycerides, fatty acids, and fatty acid esters. Oils for parenteral injection include animal, vegetable, synthetic or petroleum based oils. Examples of sugars for solution include sucrose, lactose, dextrose, mannose, and the like. Examples of oils include mineral oil, petrolatum, soybean, corn, cottonseed, peanut, and the like. Examples of fatty acids and esters include oleic acid, myristic acid, stearic acid, isostearic acid, and esters thereof.

For transdermal administration, the compounds of the invention are combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compound/enhancer compositions also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

The present invention also provides articles of manufacture for treating and preventing disorders, such as viral disorders, in a subject. The articles of manufacture comprise a pharmaceutical composition of the compounds of formula I, optionally further containing at least one additional antiviral compound, as described herein. The articles of manufacture are packaged with indications for various disorders that the pharmaceutical compositions are capable of treating and/or preventing. For example, the articles of manufacture comprise a unit dose of a compound disclosed herein that is capable of treating or preventing a certain disorder, and an indication that the unit dose is capable of treating or preventing a certain disorder, for example a viral infection.

In accordance with a method of the present invention, the compounds of formula I are administered to the subject (or are contacted with cells of the subject) in an amount effective to limit or prevent a decrease in the level of virus in the subject, particularly in cells of the subject. This amount is readily determined by the skilled artisan, based upon known procedures, including analysis of titration curves established in vivo and methods and assays disclosed herein. In one embodiment, a suitable amount of the compounds of the invention effective to limit or prevent a decrease in the level of viral particles in the subject ranges from about 0.01 mg/kg/day to about 1000 mg/kg/day, and/or is an amount sufficient to achieve plasma levels ranging from about 300 ng/mL to about 1000 ng/mL or greater. In an embodiment, the amount of compounds from the invention ranges from about 10 mg/kg/day to about 1000 mg/kg/day. In another embodiment, from about 0.01 mg/kg/day to about 500 mg/kg/day is administered. In another embodiment, from about 0.01 mg/kg/day to about 300 mg/kg/day is administered. In another embodiment, from about 0.01 mg/kg/day to about 200 mg/kg/day is administered. In another embodiment, from about 0.05 mg/kg/day to about 100 mg/kg/day is administered. In another, embodiment, from about 0.05 mg/kg/day to about 50 mg/kg/day is administered. In another, embodiment, from about 0.05 mg/kg/day to about 30 mg/kg/day is administered.

The precise dose to be employed in the compositions will also depend on the route of administration, and the seriousness of the infection or disorder, and should be decided according to the judgment of the practitioner and each patient's circumstances. However, suitable effective dosage ranges for intramuscular administration are generally about 0.5 to about 1000 mg of the compound of formula I per kilogram body weight. In specific embodiments, the i.m. dose is about 500 to about 1000 mg/kg, about 300 to about 500 mg/kg, about 200 to about 300 mg/kg, about 100 to about 200 mg/kg, about 50 to about 100 mg/kg, or about 10 to about 50 mg/kg (or the equivalent doses expressed per square meter of body surface area). Alternatively, a suitable dose range for i.v. administration may be obtained using doses of about 10 to about 1000 mg, without adjustment for a patient's body weight or body surface area. Oral compositions can contain about 10% to about 95% by weight of one or more compound of formula I alone or in combination with another therapeutic agent. In specific embodiments of the invention, suitable dose ranges for oral administration are generally about 10 to about 1000 mg, preferably about 30 to about 500 mg of compound per kilogram body weight or their equivalent doses expressed per square meter of body surface area. In specific embodiments the oral dose is about 10 to about 50 mg/kg, about 50 to about 80 mg/kg, about 80 to about 150 mg/kg, about 150 to about 250 mg/kg, about 250 to about 350 mg/kg, about 350 to about 450 mg/kg, about 450 to about 550 mg/kg, about 550 to about 700 mg/kg, about 700 to about 1000 mg/kg (or the equivalent doses expressed per square meter of body surface area). In another embodiment, a suitable dose range for oral administration, from about 20 to about 2000 mg, without adjustment for a patient's body weight or body surface area. Other effective doses may be extrapolated from dose-response curves derived from in vitro or animal model test systems. Such animal models and systems are well known in the art.

In certain aspects, an "effective amount" of a compound in the context of a viral infection is an amount sufficient to reduce one or more of the following steps of a the life cycle of a virus: the docking of the virus particle to a cell, the introduction of viral genetic information into a cell, the expression of viral proteins, the production of new virus particles and the release of virus particles from a cell by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In another specific embodiment, an effective amount of a compound in the context of a viral infection reduces the replication, multiplication or spread of a virus by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

Compounds of the present invention may be produced by the following exemplary methods.

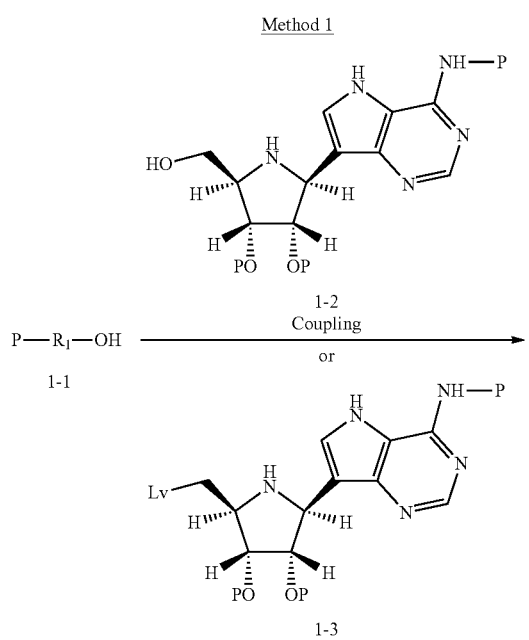

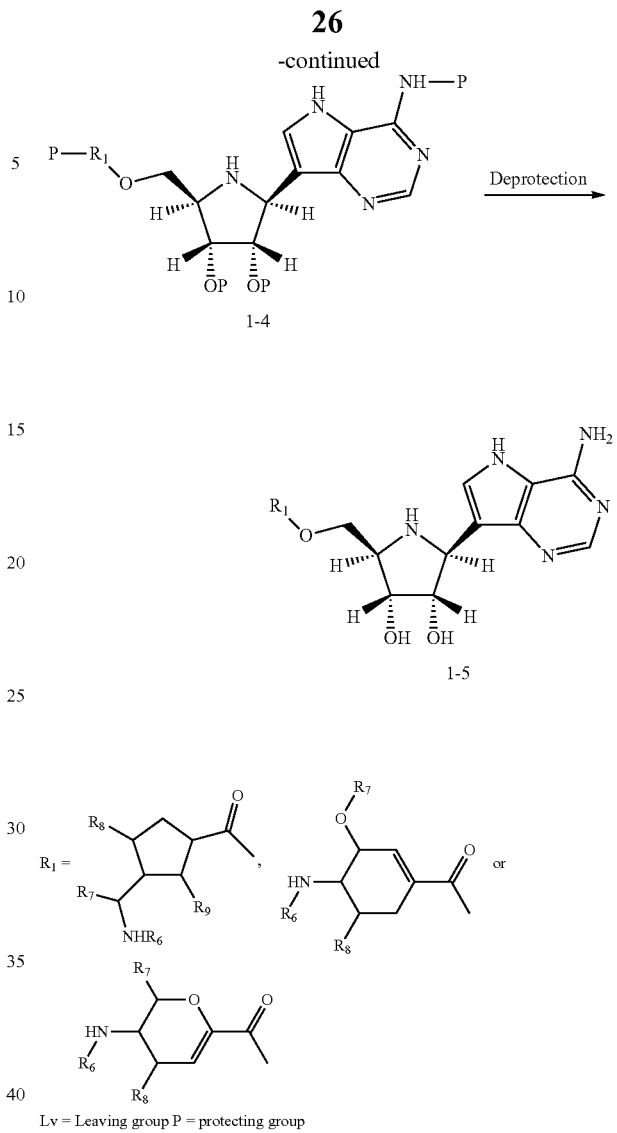

The Compounds 1-1 wherein $R_1$ is as shown may be synthesized, for example according to the methods and examples provided herein and, for example, in U.S. Pat. Nos. 5,360,817; 5,648,379; 5,866,601; 5,952,375; 6,294,572; 6,495,711; 6,503,745; or 6,562,861; the entire contents of which are incorporated by reference. Compound 1-1 wherein the compound is an acid is coupled with the alcohol (1-2) in the presence of, for example a coupling agent. Alternatively, compound 1-1 wherein the compound is an alcohol is alkylated with analog of compound 1-2 containing a leaving group. Exemplary coupling agents, leaving groups and methods are known in the art, and are described, for example in Richard C. Larock, *Comprehensive Organic Transformations: A Guide to Functional Group Preparations*, 2$^{nd}$ Ed., John Wiley & Sons, New York (1999); and Michael B. Smith & Jerry March, *March's Advanced Organic Chemistry: Reactions, Mechanisms, and Structure*, 6$^{th}$ Ed., John Wiley & Sons, New York (2007). Following the coupling, removal of the protecting groups is performed according to standard methods, such as those described, for example, in Peter G. M. Wuts & Theodora W. Greene, *Protective Groups in Organic Synthesis*, 4$^{th}$ Ed., Wiley Interscience, New York (2006).

Method 2

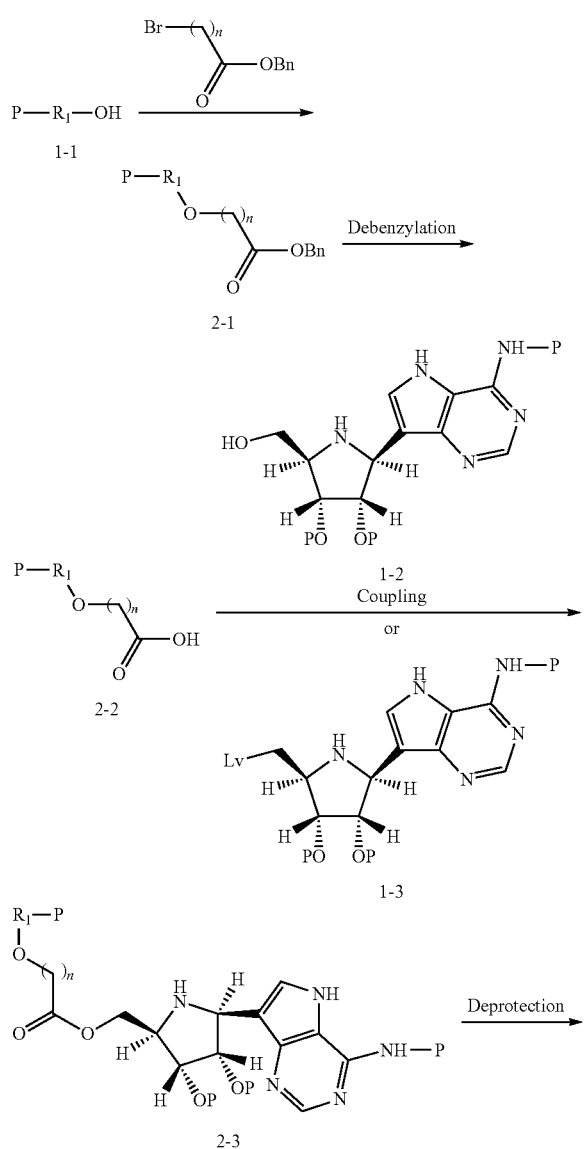

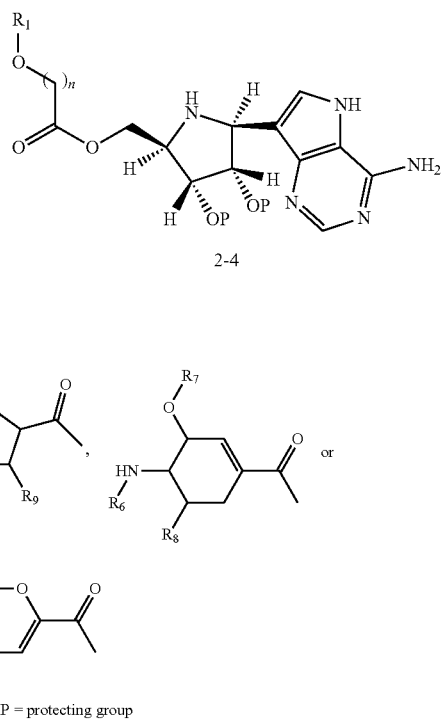

Compound 1-1 wherein the compound is an alcohol is alkylated with, for example a terminal halide or any other alkylating agent containing a leaving group as discussed above. Following the alkylation, compound 2-1 may be debenzylated via hydrogenation, for example, to generate the acid. The acid may be transformed as in Method 1 above to provide compound 2-3. Similar to Method 1, removal of the protecting groups may be performed to generate compound 2-4.

Method 3

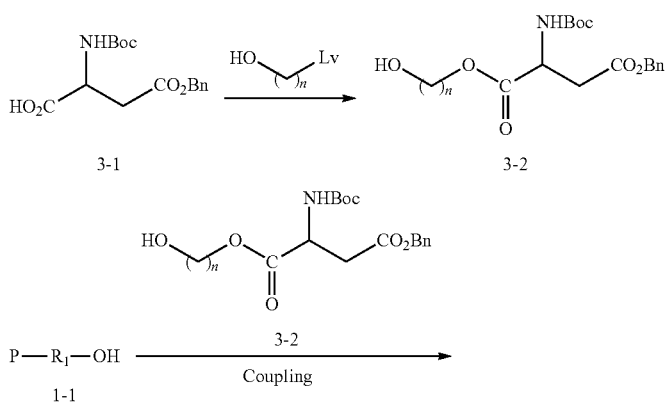

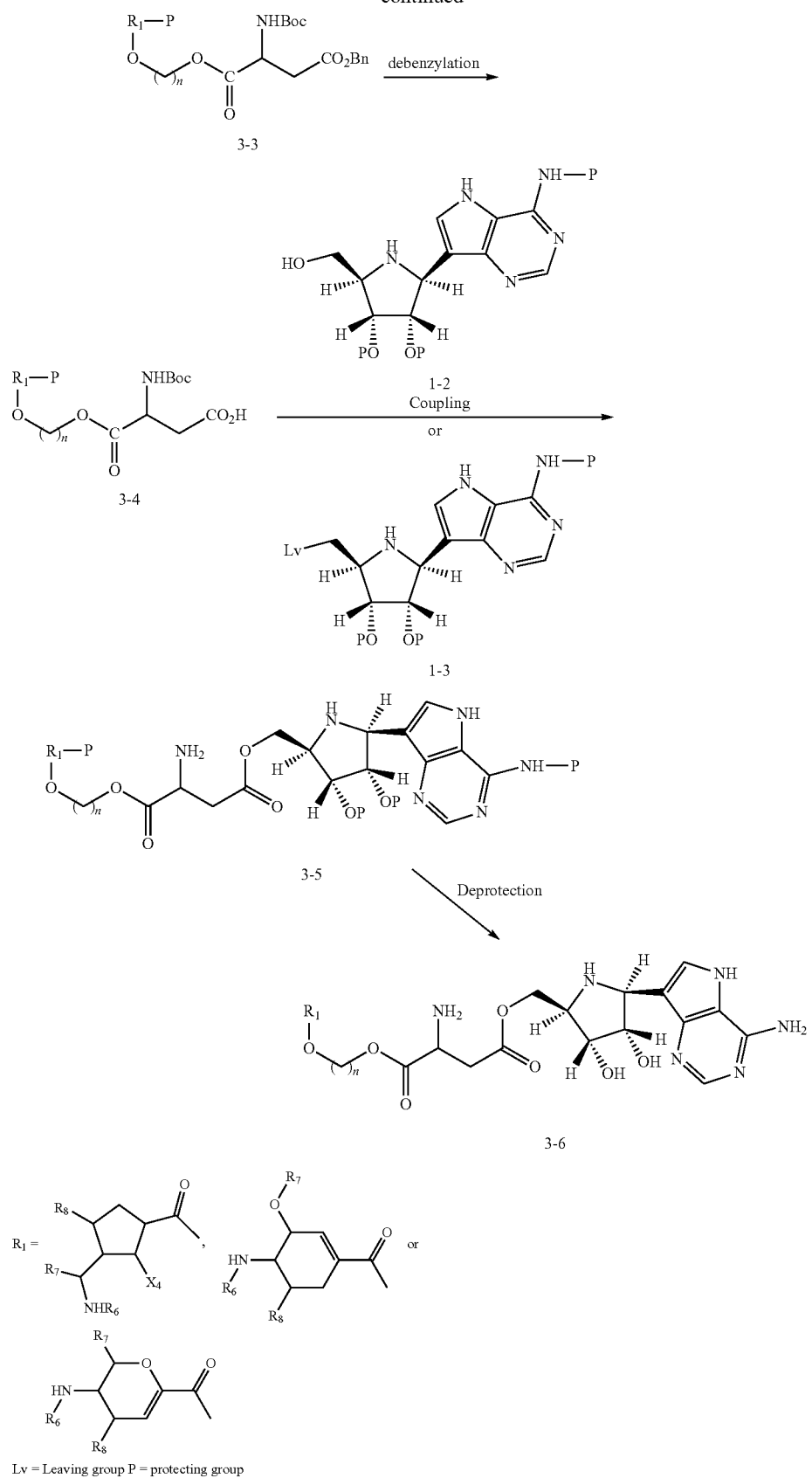

Compound 3-2 may be synthesized according to the methods provided in, for example, Cantacuzene et al., *Tetrahedron* 1989, 45(3), 741-748. Following steps similar to those disclosed in the above methods and following examples, compound 3-6 may be synthesized.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Example 1

Synthesis of (1S,2S,3R,4R)-3-((S)-1-acetamido-2-ethylbutyl)-4-(2,3-bis(tert-butoxycarbonyl)guanidino)-2-hydroxycyclopentanecarboxylic acid (4-5)

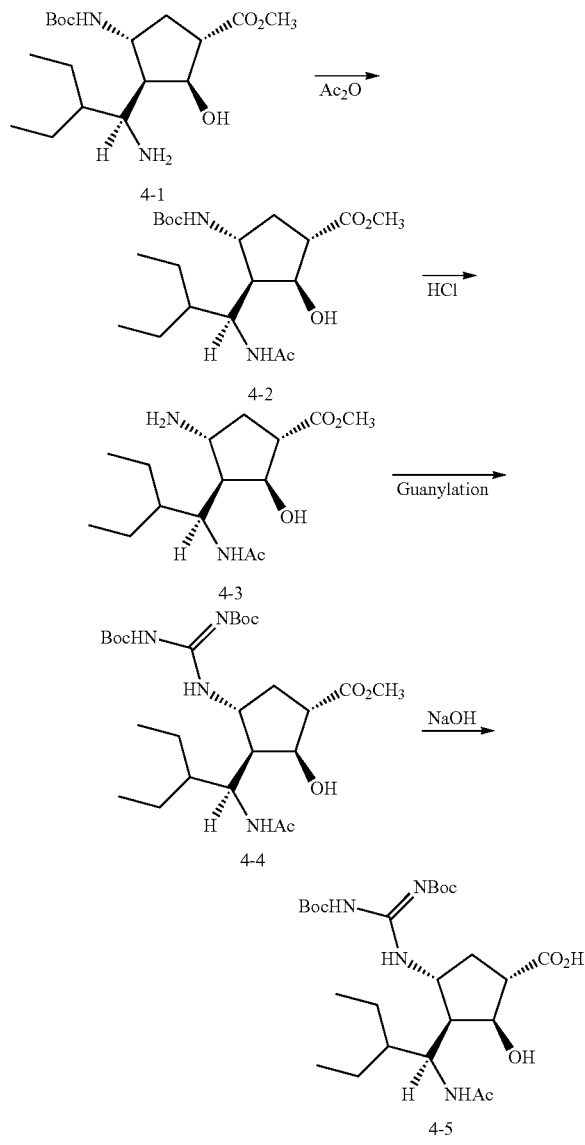

Step-1

Compound (1S,2S,3S,4R)-methyl 3-((S)-1-amino-2-ethylbutyl)-4-(tert-butoxycarbonylamino)-2-hydroxycyclopentanecarboxylate (4-1) [(prepared according to the procedure as reported by Chand, Pooran; Kotian, Pravin L.; Dehghani, Ali; El-Kattan, Yahya; Lin, Tsu-Hsing; Hutchison, Tracy L.; Babu, Y. Sudhakar; Bantia, Shanta; Elliott, Arthur J.; Montgomery, John A. in *J. Med. Chem.* 2001, 44(25), 4379-4392) 21.16 g, 0.060 mol] was suspended in toluene (88 g) and cooled to 0-5° C. Acetic anhydride (7 g, 69 mmol) was added over 10 min. at 0-30° C. The reaction mixture was stirred for 1 h at RT and then extracted with a solution of sodium carbonate (5 g, 47 mmol) in water (50 mL). The organic phase was concentrated to dryness to give (1S,2S,3R,4R)-methyl 3-((S)-1-acetamido-2-ethylbutyl)-4-(tert-butoxycarbonylamino)-2-hydroxycyclopentanecarboxylate (4-2) of product as white solid; MS (ES$^+$) 401.48, (M+1).

Step-2

To a solution of (1S,2S,3R,4R)-methyl 3-((S)-1-acetamido-2-ethylbutyl)-4-(tert-butoxycarbonylamino)-2-hydroxycyclopentanecarboxylate (4-2) (800.8 g, 2 mol) in methanol (4 L) was added dropwise conc. HCl (380 mL) and stirred at room temperature for 2 h. The reaction mixture was concentrated in vacuo to dryness to furnish after drying (1S,2S,3R,4R)-methyl 3-((S)-1-acetamido-2-ethylbutyl)-4-amino-2-hydroxycyclopentane carboxylate (4-3) (714 g, 98%) as a white solid; mp. 100-105° C. $^1$H NMR (DMSO-$d_6$): δ 0.85 (m, 6H), 1.07 (m, 2H), 1.28 (m, 2H), 1.49 (m, 1H), 1.78 (m, 2H), 1.90 (s, 3H), 2.33 (m, 2H), 2.74 (m, 1H), 3.38 (m, 1H), 3.58 (m, 1H), 4.23 (m, 2H), 6.42 (br s, 2H), 7.95 (d, J=10 Hz, 1H), 8.16 (m, 3H); IR (KBr) 3364, 2963, 1712, 1651, 1542, 1439, 1371, 1209, 1180 cm$^{-1}$; MS (ES$^+$): 301.43 (100% M+1).

Step-3

To a solution of (1S,2S,3R,4R)-methyl 3-((S)-1-acetamido-2-ethylbutyl)-4-amino-2-hydroxycyclopentanecarboxylate (4-3) (53.39 g, 75 mmol) in dry DMF (150 mL) was added Et$_3$N (31.5 mL, 225 mmol), 1,3-bis(tert-butoxycarbonyl)-2-methyl-2-thiopseudourea (26.15 g, 90 mmol) and HgCl$_2$ (24.44 g, 90 mmol). The reaction mixture was stirred overnight at room temperature and was diluted with EtOAc (250 mL). The reaction mixture was filtered through Celite and the filtrate was washed with water (2×250 mL), brine (100 mL), dried (MgSO$_4$) and concentrated in vacuo to furnish 50 g crude product. The crude was purified by flash column chromatography (silica gel, 1 kg, 0-100% EtOAc in hexane) to furnish (1S,2S,3R,4R)-methyl 3-((S)-1-acetamido-2-ethylbutyl)-4-(2,3-bis(tert-butoxycarbonyl) guanidino)-2-hydroxycyclo pentanecarboxylate (4-4) (15.8 g, 39%) as a white foam. $^1$H NMR (300 MHz, DMSO) δ 11.48 (s, 1H), 8.26 (d, J=7.9, 1H), 7.37 (d, J=10.0, 1H), 5.24 (d, J=5.1, 1H), 4.44-4.31 (m, 1H), 4.20 (t, J=8.6, 1H), 4.11 (m, 1H), 3.62 (s, 3H), 2.76-2.67 (m, 1H), 2.07-1.99 (m, 1H), 1.71 (s, 3H), 1.55 (dd, J=5.1, 11.9, 1H), 1.62-1.53 (m, 1H), 1.52-1.32 (m, 2H), 1.48 (s, 9H), 1.39 (s, 9H), 1.31-1.2 (m, 1H), 1.11-0.92 (m, 2H), 0.84 (q, J=7.2, 6H); MS (ES$^-$) 541.1.

Step-4

To a solution of (1S,2S,3R,4R)-methyl 3-((S)-1-acetamido-2-ethylbutyl)-4-(2,3-bis(tert-butoxycarbonyl)guanidino)-2-hydroxycyclopentanecarboxylate (4-4) (15.8 g, 29 mmol) in methanol (60 mL) and THF (60 mL) was added 1 N NaOH (60 mL, 60 mmol). The reaction mixture was stirred at room temp for 2 h and concentrated in vacuo to remove methanol and THF. The aqueous layer was acidified with HCl (40 mL, 1 N) to pH 4 and the solid obtained was collected by filtration washed with ether to furnish on drying (1S,2S,3R,4R)-3-((S)-1-acetamido-2-ethylbutyl)-4-(2,3-bis(tert-butoxycarbonyl)guanidino)-2-hydroxycyclo pentanecarboxylic acid (4-5) (12.53 g, 81%) as a white foam. $^1$H NMR (300 MHz, CDCl$_3$) δ 11.40 (s, 1H), 8.75 (d, J=8.7, 1H), 8.61 (d, J=7.9, 1H), 4.51-4.43 (m, 1H), 4.40-4.36 (m, 1H), 4.04-3.94 (m, 1H), 2.89-2.81 (m, 1H), 2.62-2.47 (m, 1H), 2.14 (s, 3H), 1.92 (d, J=8.6, 1H), 1.90-1.83 (m, 1H), 1.51 (m, 10H), 1.49 (m, 13H), 0.99-0.87 (m, 2H), 0.79 (dt, J=7.2, 14.4, 6H); MS (ES$^+$) 530.2 (M+1), 551.2 (M+Na); (ES$^-$) 527.0 (M-1)

Example 2

Synthesis of (2S,3S,4R,5R)-2-(4-Amino-5H-pyrrolo[3,2-d]pyrimidin-7-yl)-5-(hydroxymethyl)pyrrolidine-3,4-diol(5-8: the HCl salt of compound 1, wherein compound 1 is compound A wherein R$_4$ is NH$_2$ and R$_5$ is hydrogen)

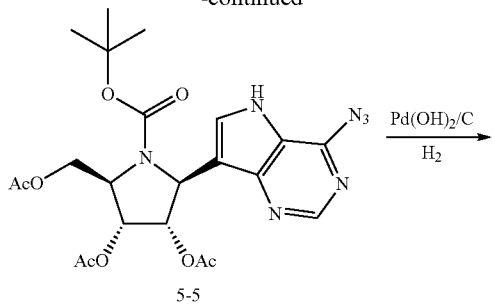

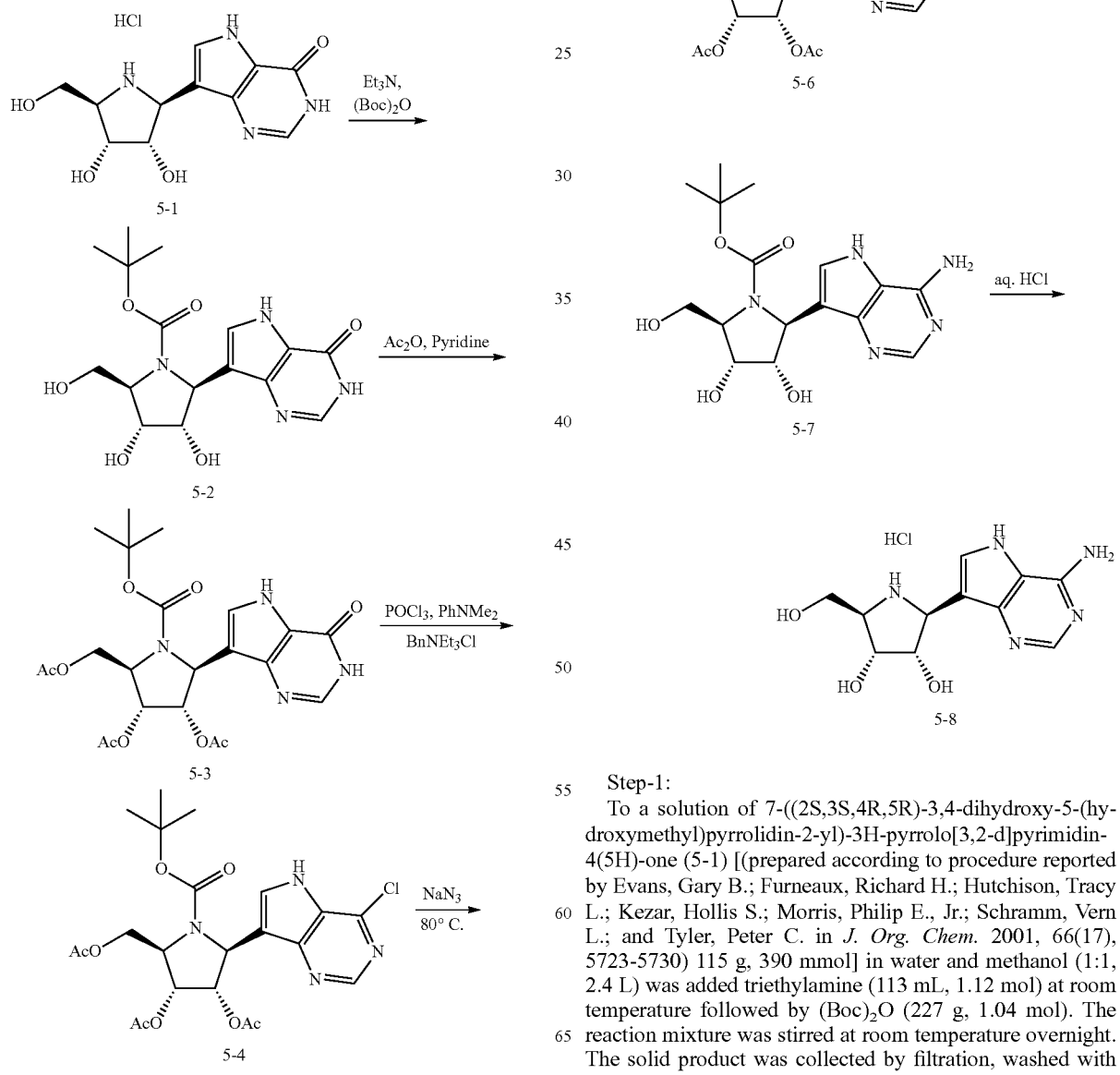

Step-1:

To a solution of 7-((2S,3S,4R,5R)-3,4-dihydroxy-5-(hydroxymethyl)pyrrolidin-2-yl)-3H-pyrrolo[3,2-d]pyrimidin-4(5H)-one (5-1) [(prepared according to procedure reported by Evans, Gary B.; Furneaux, Richard H.; Hutchison, Tracy L.; Kezar, Hollis S.; Morris, Philip E., Jr.; Schramm, Vern L.; and Tyler, Peter C. in *J. Org. Chem.* 2001, 66(17), 5723-5730) 115 g, 390 mmol] in water and methanol (1:1, 2.4 L) was added triethylamine (113 mL, 1.12 mol) at room temperature followed by (Boc)$_2$O (227 g, 1.04 mol). The reaction mixture was stirred at room temperature overnight. The solid product was collected by filtration, washed with water, and dried under vacuum to afford (2R,3R,4S,5S)-tertbutyl 3,4-dihydroxy-2-(hydroxymethyl)-5-(4-oxo-4,5-dihydro-3H-pyrrolo[3,2-d]pyrimidin-7-yl)pyrrolidine-1-carboxylate (5-2) (100%) as a white solid. $^1$H NMR (300 MHz, DMSO) δ 7.85 (s, 1H), 7.35 (s, 1H), 4.73-4.53 (m, 1H), 4.29 (s, 1H), 4.03 (s, 1H), 3.97 (s, 1H), 3.70-3.53 (m, 2H), 1.36 and 1.04 (s, 3H, 6H for rotomers).

Step-2:

To a solution of (2R,3R,4S,5S)-tert-butyl 3,4-dihydroxy-2-(hydroxymethyl)-5-(4-oxo-4,5-dihydro-3H-pyrrolo[3,2-d]pyrimidin-7-yl)pyrrolidine-1-carboxylate (5-2) in pyridine (184 mmol, 2.26 mol) was added DMAP (0.79 g, 6.46 mmol) and acetic anhydride (107 mL, 1131 mmol) at room temperature. The reaction mixture was stirred at room temperature overnight. The reaction mixture was diluted with chloroform and washed with water, aqueous HCl, water, and aqueous saturated sodium bicarbonate. The organic layer was dried, filtered, and concentrated under vacuum to furnish (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (5-3) (150 g), which was pure enough to be used as such for next step. MS (ES$^+$) 493.1 (M+1), 515.1 (M+Na); (ES$^-$) 491.4 (M−1).

Step-3:

To a solution of (2R,3R,4S,5S)-2-(acetoxymethyl)-1-(tert-butoxycarbonyl)-5-(4-oxo-4,5-dihydro-3H-pyrrolo[3,2-d]pyrimidin-7-yl)pyrrolidine-3,4-diyl diacetate (5-3) (150 g, 300 mmol) in acetonitrile (660 mL) was added benzyltriethylammonium chloride (137 g, 600 mmol), dimethylaniline (57 mL, 450 mmol), followed by POCl$_3$ (164 mL, 1800 mmol) at room temperature. The reaction mixture was heated at 80° C. for 1 h. The reaction mixture was cooled to room temperature and concentrated to dryness under vacuum. The residue obtained was dissolved in chloroform and washed with aqueous saturated sodium bicarbonate, brine, dried, filtered and concentrated to dryness. The residue of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (5-4) was used as such in next step without purification. $^1$H NMR (300 MHz, DMSO) δ 12.54 (s, 1H), 8.65 (s, 1H), 7.92 (s, 1H), 5.85 (m, 1H), 5.45 (m, 1H), 5.10 (m, 1H), 4.49 (m, 2H), 4.07 (m, 1H), 2.07-1.99 (m, 9H), 1.19 (2 bs, 9H, rotomers).

Step-4:

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (5-4) (300 mmol) in DMF (540 mL) was added sodium azide (97.5 g, 1500 mmol) and heated at 80° C. overnight. The reaction mixture was concentrated under vacuum and the residue obtained was dissolved in chloroform. The chloroform layer was washed with water, dried, filtered and concentrated under vacuum. Purification by crystallization from (acetone: hexane=1:2) furnished (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (5-5). $^1$H NMR (300 MHz, DMSO) δ 13.56-13.00 (bs, 1H), 9.86 (s, 1H), 7.95 (s, 1H), 5.78 (m, 1H), 5.40 (m, 1H), 5.26-5.14 (m, 1H), 4.54 (m, 1H), 4.42 (m, 1H), 4.16-4.03 (m, 1H), 2.06 (s, 3H), 2.02 (s, 6H), 1.14 (bs, 9H); MS (ES$^+$) 540.0 (M+1); (ES$^-$) 515.9 (M−1).

Step-5:

To a solution of (2R,3R,4S,5S)-2-(acetoxymethyl)-5-(4-azido-5H-pyrrolo[3,2-d]pyrimidin-7-yl)-1-(tert-butoxycarbonyl)pyrrolidine-3,4-diyl diacetate (5-5) (300 mmol) in methanol (1 L) was added Pd(OH)$_2$ (30 g). The reaction mixture was hydrogenated at (160 psi) overnight, and filtered to remove catalyst through Celite. The filtrate was concentrated under vacuum to furnish (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (5-6) (113 g). $^1$H NMR (300 MHz, DMSO) δ 12.47-11.92 (m, 1H), 8.84-8.03 (m, 3H), 7.90-7.68 (m, 1H), 5.70-5.51 (m, 1H), 5.38 (m, 1H), 5.12 (m, 1H), 4.42 (m, 2H), 4.17-4.00 (m, 1H), 2.07 (s, 3H), 2.05 (s, 3H), 2.00 (s, 3H), 1.14 (s, 9H); MS (ES$^+$) 492.1 (M+1), (ES$^-$) 490.0 (M−1).

Step-6:

To a solution of (2R,3R,4S,5S)-2-(acetoxymethyl)-5-(4-amino-5H-pyrrolo[3,2-d]pyrimidin-7-yl)-1-(tert-butoxycarbonyl)pyrrolidine-3,4-diyl diacetate (5-6) (111 g, 226 mmol) in methanol (500 mL) was added NaOMe (25% w/w in methanol, 4.88 g, 22.6 mmol) at room temperature. The reaction mixture was stirred at room temperature for 3 h and concentrated under vacuum to give (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (5-7). $^1$H NMR (300 MHz, DMSO) δ 11.40-10.73 (bs, 1H), 8.01 (s, 1H), 7.39 (2s, 1H), 6.90 (s, 2H), 4.83 (m, 2H), 4.45 (m, 2H), 3.96 (s, 2H), 3.58 (m, 3H), 1.31 and 0.99 (s, 3H, 6H, rotomers); MS (ES$^+$) 366.0 (M+1), 388.0 (M+Na); (ES$^-$) 363.8 (M−1).

Step-7:

A solution of (2S,3S,4R,5R)-tert-butyl 2-(4-amino-5H-pyrrolo[3,2-d]pyrimidin-7-yl)-3,4-dihydroxy-5-(hydroxymethyl)pyrrolidine-1-carboxylate (5-7) aqueous HCl (160 mL of conc. HCl and 400 mL of water) was stirred at room temperature for 30 min and then concentrated under vacuum to dryness. The residue obtained was dissolved in water, treated with activated charcoal and refluxed for 30 min. The hot solution was filtered through Celite and concentrated under vacuum to obtain a semi-solid product, which was recrystallized from water and ethanol to furnish (2S,3S,4R,5R)-2-(4-amino-5H-pyrrolo[3,2-d]pyrimidin-7-yl)-5-(hydroxymethyl)pyrrolidine-3,4-diol (5-8) (50 g, overall yield for 7 steps: 42.6%) as white crystal. $^1$H NMR (300 MHz, D$_2$O) δ 8.41 (s, 1H), 8.02 (s, 1H), 4.99 (d, J=9 Hz, 1H), 4.78 (m, 1H), 4.45 (dd, J=3, 1.5 Hz, 1H), 3.97 (m, 2H), 3.90 (m, 1H); MS (ES$^+$) 266.2 (M+1), (ES$^-$) 264.0 (M−1); Analysis: Calculated for C$_{11}$H$_{15}$N$_5$O$_3$. 2 HCl: C, 39.07; H, 5.07; N, 20.71; Cl, 20.97. Found: C, 39.09; H, 5.10; N, 20.49; Cl, 20.84.

Example 3
Synthesis of (1S,2S,3R,4R)-((2R,3R,4S,5S)-5-(4-amino-5H-pyrrolo[3,2-d]pyrimidin-7-yl)-3,4-dihydroxypyrrolidin-2-yl)methyl 3-((S)-1-acetamido-2-ethylbutyl)-4-guanidino-2-hydroxycyclopentanecarboxylate (6-5)
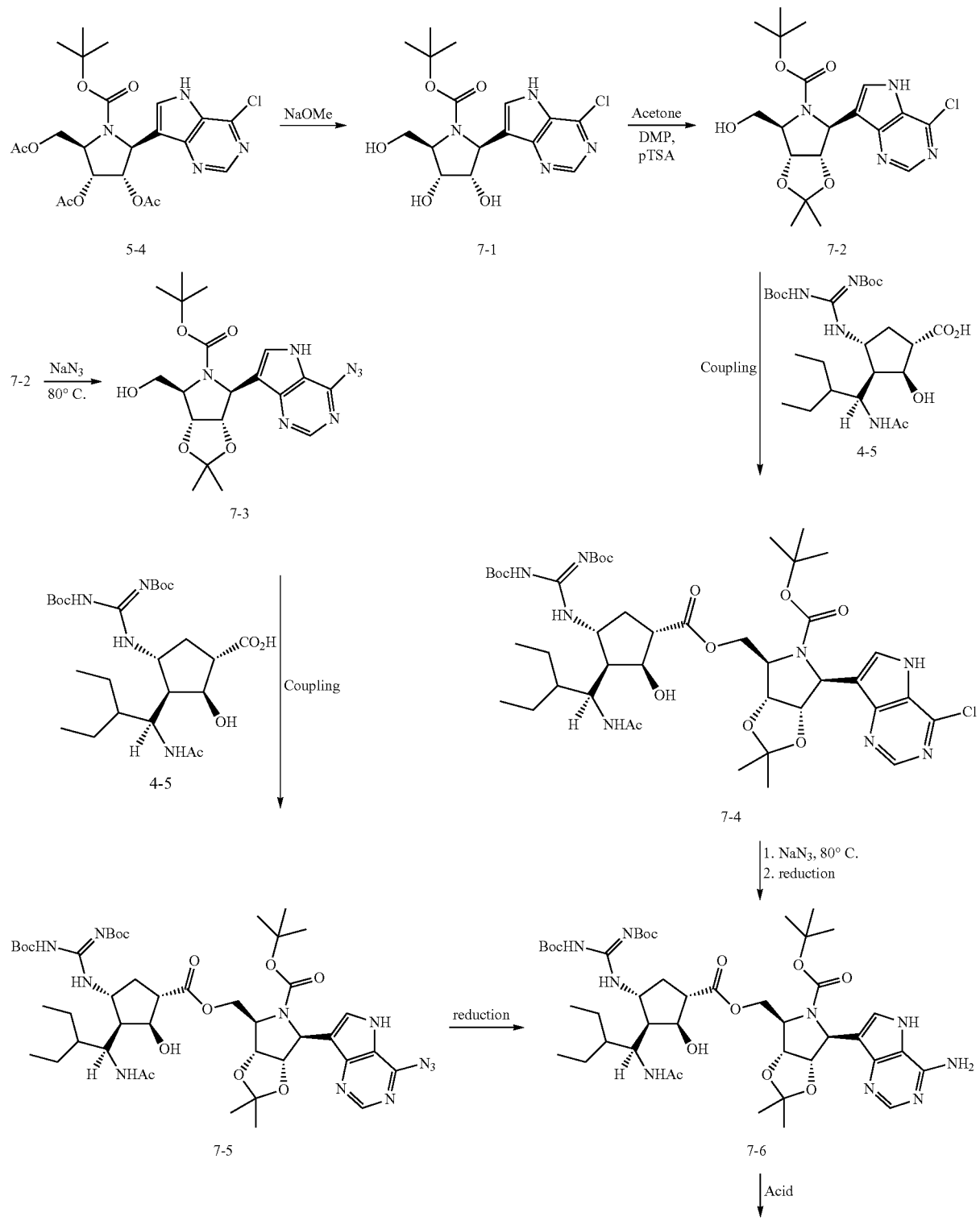

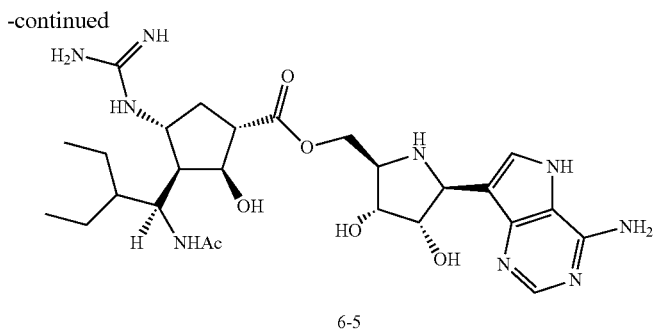

6-5

Step-1

To a solution of (2R,3R,4S,5S)-2-(acetoxymethyl)-1-(tert-butoxycarbonyl)-5-(4-chloro-5H-pyrrolo[3,2-d]pyrimidin-7-yl)pyrrolidine-3,4-diyl diacetate (5-4) (15 g, 30 mmol) in 150 mL of methanol was added NaOMe (25% w/w solution in methanol, 2.28 mL, 10 mmol) at room temperature. The reaction mixture was stirred at room temperature overnight and concentrated under vacuum to dryness. The residue obtained was purified by flash column chromatography (silica gel, eluting with methanol in chloroform 0 to 10%) to afford product (2S,3S,4R,5R)-tert-butyl 2-(4-chloro-5H-pyrrolo[3,2-d]pyrimidin-7-yl)-3,4-dihydroxy-5-(hydroxymethyl)pyrrolidine-1-carboxylate (7-1) (9 g, 79%) as a foam. $^1$H NMR (300 MHz, DMSO) δ 12.33 (s, 1H), 8.62 (s, 1H), 7.94 (s, 1H), 5.32 (s, 1H), 5.04 (s, 1H), 4.88 (s, 2H), 4.33 (s, 1H), 4.06 (s, 1H), 4.02-3.93 (m, 1H), 3.69-3.53 (m, 2H), 1.35 and 1.01 (2s, 3H and 6H for rotamers);

Step-2

To the solution of (2S,3S,4R,5R)-tert-butyl 2-(4-chloro-5H-pyrrolo[3,2-d]pyrimidin-7-yl)-3,4-dihydroxy-5-(hydroxymethyl)pyrrolidine-1-carboxylate (7-1) (9 g, 23.4 mmol) in acetone (250 mL) was added DMP (6.1 mL, 50 mmol) and p-toluenesulfonic acid monohydrate (220 mg, 1.17 mmol). The reaction mixture was stirred at room temperature until complete by TLC analysis. The reaction was made basic by adding Et$_3$N and concentrated under vacuum to dryness. The residue obtained was purified by flash column chromatography to afford (3aS,4S,6R,6aR)-tert-butyl 4-(4-chloro-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (7-2) (10.3 g, 100%) as a white foam. $^1$H NMR (300 MHz, DMSO) δ 12.59-12.23 (bs, 1H), 8.67 (s, 1H), 7.79 (s, 1H), 5.16 (m, 3H), 3.99 (m, 1H), 3.42 (m, 3H), 1.47 (s, 3H), 1.29 (s, 3H), 1.38-1.20 (bs, 9H).

Step-3

To the solution of (3aS,4S,6R,6aR)-tert-butyl 4-(4-chloro-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (7-2) (5.1 g, 12 mmol) in DMF (30 mL) was added sodium azide (3.9 g, 60 mmol) and heated at 80° C. for 4 h. The reaction mixture was concentrated under vacuum to remove DMF and the residue obtained was dissolved in chloroform. The chloroform layer was washed with water, dried, filtered and concentrated under vacuum to furnish (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (7-3) (5 g, 96%). $^1$H NMR (300 MHz, DMSO) δ 13.36-13.08 (bs, 1H), 9.87 (s, 1H), 7.69-7.47 (m, 1H), 5.28 (m, 1H), 5.05 (m, 2H), 4.81 (d, J=5.9, 1H), 4.06-3.91 (m, 1H), 3.57 (m, 1H), 3.51-3.38 (m, 1H), 1.48 (s, 3H), 1.41-1.23 (bs, 9H), 1.30 (s, 3H); MS (ES$^+$) 454 (M+Na), 863.1 (2M+1), 885.2 (2M+Na); (ES$^-$) 429.7 (M−1).

Step-4

To the solution of (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (7-3) (500 mg, 1.16 mmol) and (1S,2S,3R,4R)-3-((S)-1-acetamido-2-ethylbutyl)-4-(2,3-bis(tert-butoxycarbonyl)guanidino)-2-hydroxycyclopentanecarboxylic acid (4-5) (529 mg, 1.0 mmol) in the mixture of DMF and DCM (5 mL and 30 mL) was added EDCI (960 mg, 5.0 mmol) and DMAP (37 mg, 0.3 mmol). The reaction mixture was stirred at room temperature for 4 days. The reaction mixture was quenched with water (20 mL) and the organic layer was separated. The organic layer was washed with brine, dried, filtered and concentrated under vacuum. The residue obtained was purified by flash column chromatography [silica gel, twice eluting with (9:1) ethyl acetate/methanol in hexane 0 to 100%] to afford (3aR,4R,6S,6aS)-tert-butyl 4-((((1S,2S,3R,4R)-3-((S)-1-acetamido-2-ethylbutyl)-4-(2,3-bis(tert-butoxycarbonyl)guanidino)-2-hydroxycyclopentanecarbonyl)oxy)methyl)-6-(4-azido-5H-pyrrolo[3,2-d]pyrimidin-7-yl)-2,2-dimethyldihydro-3aH-[1,3]dioxolo[4,5-c]pyrrole-5(4H)-carboxylate (7-5) (90 mg 10%) as a white solid. $^1$H NMR (300 MHz, MeOD) δ 9.62 (s, 1H), 7.98 (s, 1H), 7.60 (s, 1H), 5.41 (m, 1H), 5.38-5.26 (m, 1H), 4.25 (m, 6H), 2.71-2.63 (m, 1H), 2.57-2.43 (m, 1H), 2.21-2.11 (m, 1H), 2.01 (s, 3H), 1.99 (s, 1H), 1.81-1.67 (m, 1H), 1.50 (m, 30H), 1.37 (s, 3H), 1.20-1.06 (m, 3H), 0.99-0.86 (m, 9H); MS (ES$^+$) 943.4 (M+1), 964.3 (M+Na), (ES$^-$) 940.5 (M−1).

Step-5

To a solution of (3aR,4R,6S,6aS)-tert-butyl 4-((((1S,2S,3R,4R)-3-((S)-1-acetamido-2-ethylbutyl)-4-(2,3-bis(tert-butoxycarbonyl)guanidino)-2-hydroxycyclopentanecarbonyl)oxy)methyl)-6-(4-azido-5H-pyrrolo[3,2-d]pyrimidin-7-yl)-2,2-dimethyldihydro-3aH-[1,3]dioxolo[4,5-c]pyrrole-5(4H)-carboxylate (7-5) (90 mg, 0.098 mmol) in 20 mL of methanol was added 30 mg of Pd/C (10% by wt) and stirred under hydrogen overnight. The catalyst was removed by filtration through Celite and the filtrate was concentrated under vacuum. The residue obtained was purified by flash column chromatography [silica gel 4 g, eluting with (9:1) ethyl acetate/methanol in hexane 0 to 100%] to afford (3aR,4R,6S,6aS)-tert-butyl 4-((((1S,2S,3R,4R)-3-((S)-1-acetamido-2-ethylbutyl)-4-(2,3-bis(tert-butoxycarbonyl)guanidino)-2-hydroxycyclopentanecarbonyl)oxy)methyl)-6-(4-amino-5H-pyrrolo[3,2-d]pyrimidin-7-yl)-2,2-dimethyldihydro-3aH-[1,3]dioxolo[4,5-c]pyrrole-5(4H)-carboxylate (7-6) (45 mg, 47%) as a white solid. $^1$HNMR (300 MHz, DMSO) δ 11.48 (s, 1H), 10.88 (s, 1H), 8.25 (d, 1H), 8.10 (s, 1H), 7.36 (s, 2H), 6.79 (s, 2H), 5.23 (s, 2H), 5.19-5.09 (m, 1H), 4.96-4.83 (m, 1H), 4.45-4.29 (m, 1H), 4.20 (m, 5H), 1.99 (s, 3H), 1.70 (s, 3H), 1.65-1.52 (m, 1H), 1.45 (s, 9H), 1.51-1.30 (m, 23H), 1.28 (s, 3H), 1.12-0.91 (m, 3H), 0.84 (m, 6H); MS (ES$^+$) 916.5 (M+1), (ES$^-$) 914.6 (M−1).

Step-6

To the solution of (3aR,4R,6S,6aS)-tert-butyl 4-((((1S,2S,3R,4R)-3-((S)-1-acetamido-2-ethylbutyl)-4-(2,3-bis(tert-butoxycarbonyl)guanidino)-2-hydroxycyclopentanecarbonyl)oxy)methyl)-6-(4-amino-5H-pyrrolo[3,2-d]pyrimidin-7-yl)-2,2-dimethyldihydro-3aH-[1,3]dioxolo[4,5-c]pyrrole-5(4H)-carboxylate (7-6) (43 mg, 0.047 mmol) in 10 mL of DCM was added 1 mL of TFA. The reaction mixture was stirred at room temperature for 2 h and concentrated under vacuum to dryness. The residue obtained was dissolved in a mixture of AcOH and water (3:2, 5 mL) and heated at 60° C. until complete hydrolysis of protecting groups was achieved and then concentrated under vacuum to dryness to furnish (1S,2S,3R,4R)-((2R,3R,4S,5S)-5-(4-amino-5H-pyrrolo[3,2-d]pyrimidin-7-yl)-3,4-dihydroxypyrrolidin-2-yl)methyl 3-((S)-1-acetamido-2-ethylbutyl)-4-guanidino-2-hydroxycyclopentanecarboxylate (6-5) (40 mg) as a white solid. $^1$H NMR (300 MHz, D2O) δ 8.33 (s, 1H), 7.95 (s, 1H), 4.97 (d, J=7.8, 1H), 4.56-4.30 (m, 5H), 4.04 (m, 1H), 3.85 (m, 1H), 2.96-2.80 (m, 1H), 2.55 (m, 1H), 2.09 (m, 1H), 1.91 (s, 3H), 1.78-1.66 (m, 1H), 1.39 (m, 4H), 0.97 (m, 2H), 0.85-0.76 (m, 6H); MS (ES$^+$) 576.11 (M+1), (ES$^-$) 574.18 (M−1).

Example 4

Synthesis of (1S,2S,3R,4R)-((2R,3R,4S,5S)-5-(4-amino-5H-pyrrolo[3,2-d]pyrimidin-7-yl)-3,4-dihydroxypyrrolidin-2-yl)methyl 3-((S)-1-acetamido-2-ethylbutyl)-4-guanidino-2-hydroxycyclopentanecarboxylate (6-5)

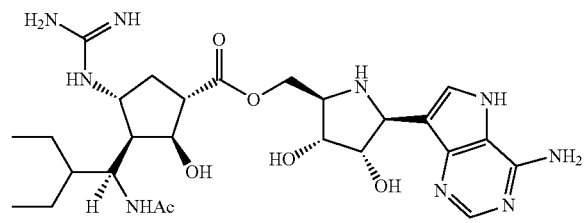 [SMILES: CCC(CC)[C@H](NC(C)=O)[C@@H]1[C@H](O)[C@@H](C(=O)OC[C@H]2N[C@@H](c3c[nH]c4c(N)ncnc34)[C@H](O)[C@@H]2O)C[C@H]1NC(=N)N]

To (3aR,4R,6S,6aS)-tert-butyl 4-((((1S,2S,3R,4R)-3-((S)-1-acetamido-2-ethylbutyl)-4-(2,3-bis(tert-butoxycarbonyl)guanidino)-2-hydroxycyclopentanecarbonyl)oxy)methyl)-6-(4-amino-5H-pyrrolo[3,2-d]pyrimidin-7-yl)-2,2-dimethyldihydro-3aH-[1,3]dioxolo[4,5-c]pyrrole-5(4H)-carboxylate (7-6) (300 mg, 0.33 mmol) was added 5 mL of trifluoroacetic acid. The reaction mixture was stirred at room temperature for 1 h and concentrated under vacuum to dryness. The residue obtained was dissolved in glacial acetic acid (10 mL) and added boron trichloride (1 M solution in dichloromethane, 1.2 mL, 1.2 mmol) and stirred at room temperature for 5 mins. The reaction mixture was concentrated under vacuum to dryness and the residue obtained was dissolved in water (5 mL). The aqueous layer was freeze dried to furnish (1 S,2S,3R,4R)-((2R,3R,4S,5S)-5-(4-amino-5H-pyrrolo[3,2-d]pyrimidin-7-yl)-3,4-dihydroxypyrrolidin-2-yl)methyl 3-((S)-1-acetamido-2-ethylbutyl)-4-guanidino-2-hydroxycyclopentanecarboxylate (6-5) (200 mg, 84%) as a white solid. $^1$H NMR (300 MHz, Acetic acid-d$_4$) δ 8.45 (s, 1H), 8.12 (s, 1H), 5.12 (m, 1H), 4.94-4.82 (m, 1H), 4.61-4.30 (m, 5H), 4.20-4.09 (m, 1H), 4.08-3.98 (m, 1H), 2.94-2.82 (m, 1H), 2.71-2.55 (m, 1H), 2.30-2.18 (m, 1H), 1.95 (s, 3H), 1.85-1.73 (m, 1H), 1.52-1.23 (m, 3H), 1.00-0.85 (m, 2H), 0.78 (m, 6H); MS (576.14 (M+1); (ES$^-$) 574.34; Elemental analysis calculated for C$_{26}$H$_{41}$N$_9$O$_6$.3 HCl.2.5H$_2$O: C, 42.77; H, 6.76; Cl, 14.57; N, 17.27. Found: C, 42.49; H, 6.65; Cl, 14.90; N, 16.93.

Example 5

Synthesis of Compound 7-4

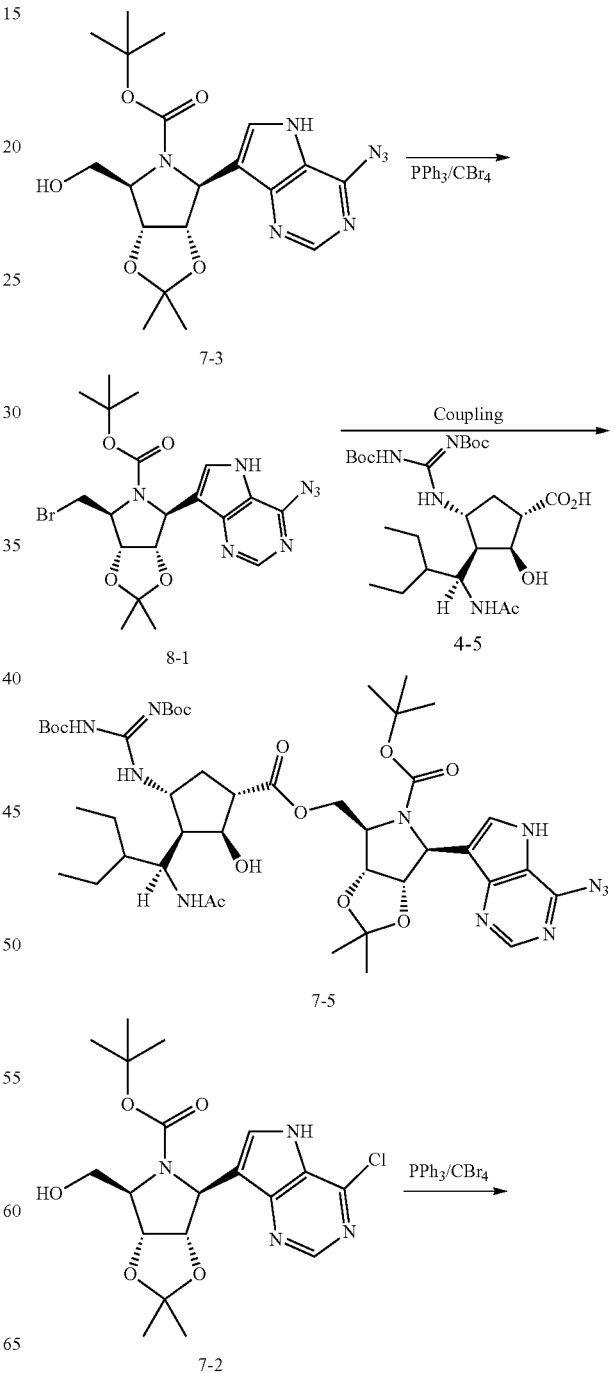

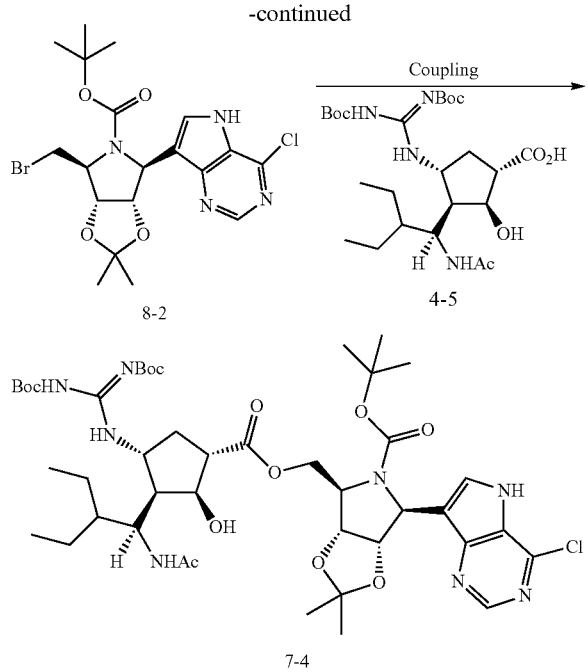

Following procedures similar to those exemplified in Example 3, compound 7-4 may be synthesized by the above scheme.

Example 6

Phosphorylation of Compound 1 (Compound A, Wherein $R_4$ is $NH_2$ and $R_5$ is H) and DNA/RNA Incorporation Studies Human hepatocellular carcinoma (Huh-7) cells were incubated with $^3$H-compound 1 for 24 hrs, followed by methanol extraction and HPLC analysis using SAX column and radioactive detector. FIG. 1 shows the phosphorylation of compound 1 in Huh-7 cells, indicating efficient phosphorylation in cells.

Figure 2:
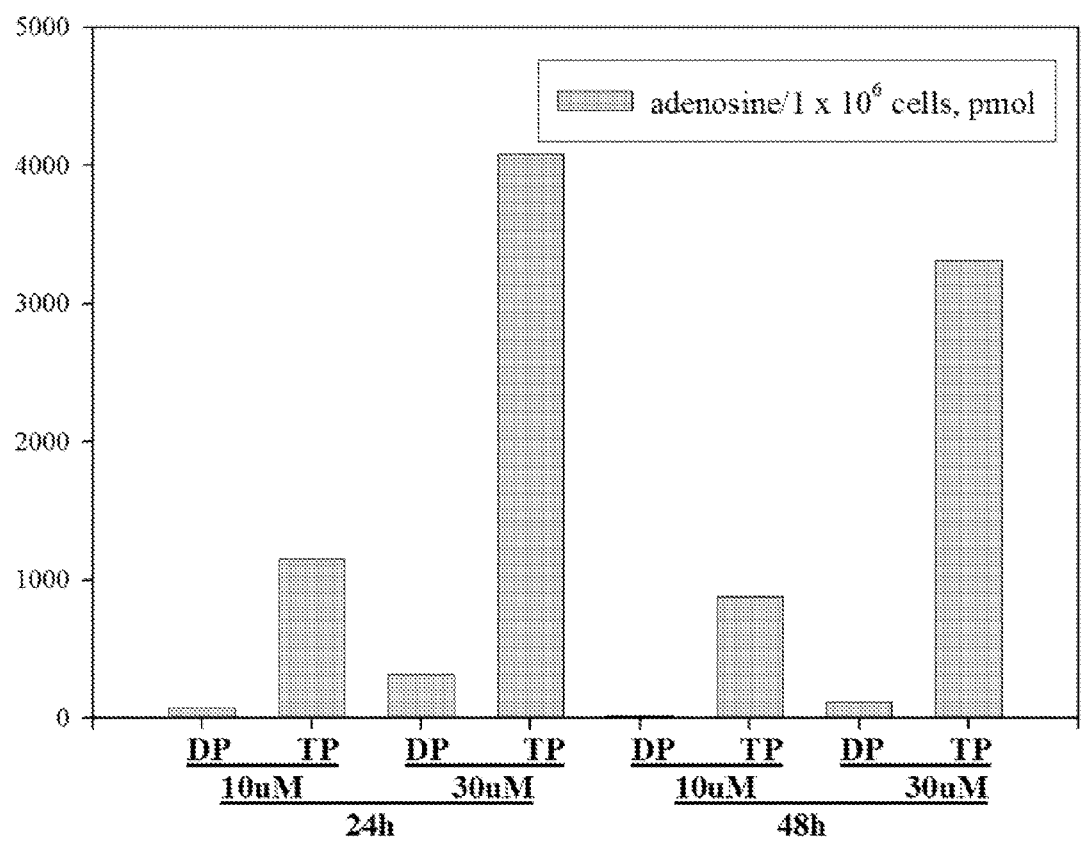
FIG. 2 shows phosphorylation of adenosine in Huh-7 cells.
Figure 3:
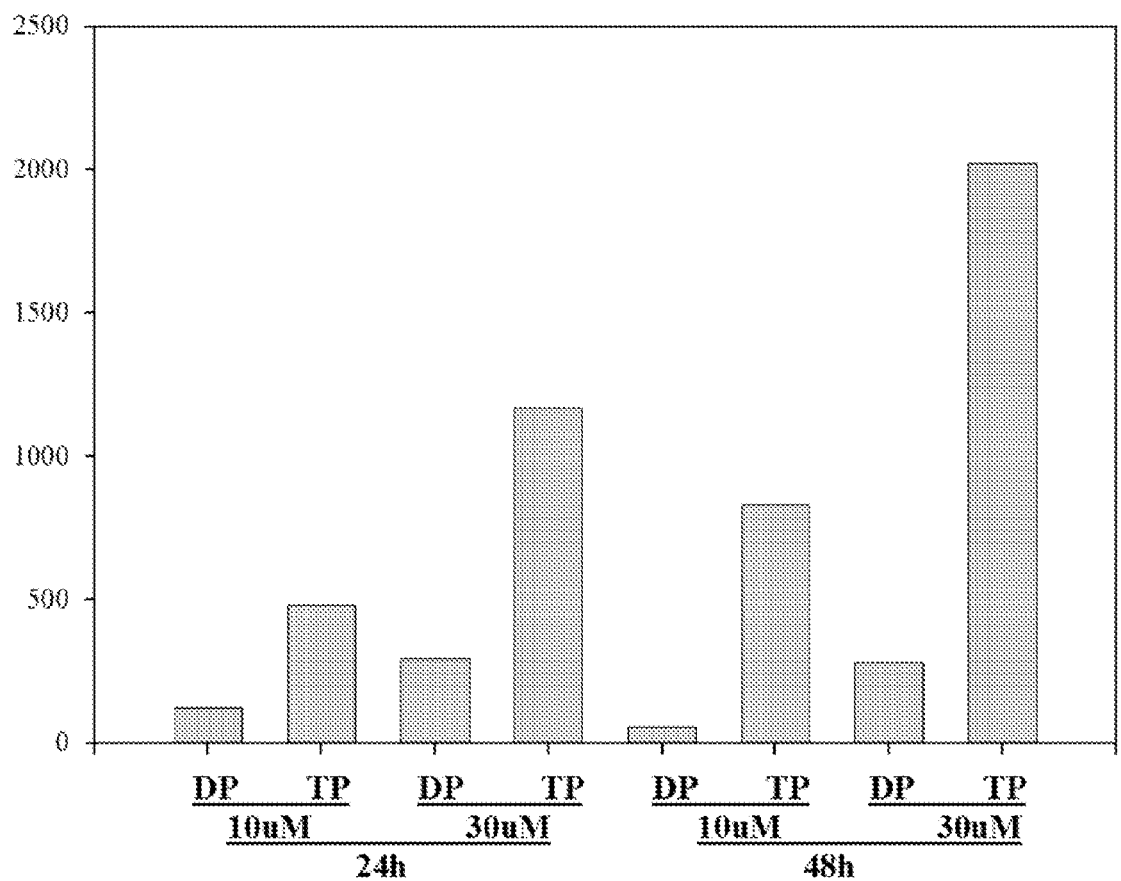
FIG. 3 shows phosphorylation of compound A in Huh-7 cells.
Figure 4:
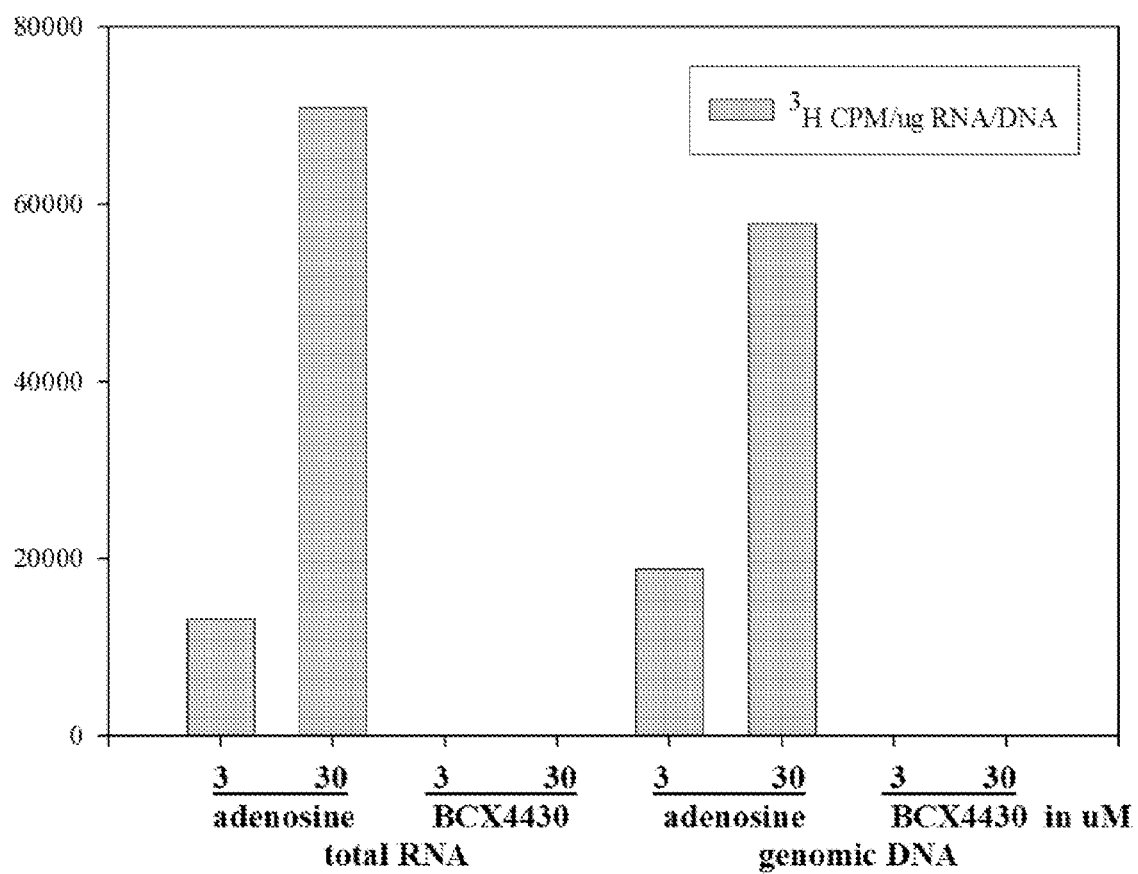
FIG. 4 shows total RNA and genomic DNA incorporation of compound 1 and adenosine in Huh-7 cells.
Figure 5:
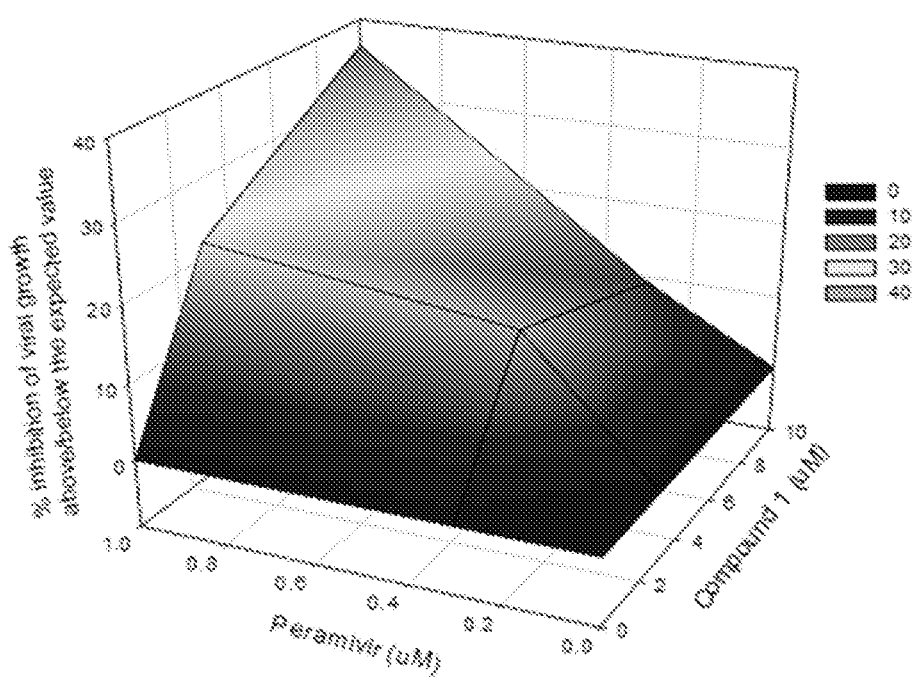
FIG. 5 shows the combination effects of compound 1 and peramivir (a neuraminidase inhibitor) on influenza in vitro.
Figure 6:
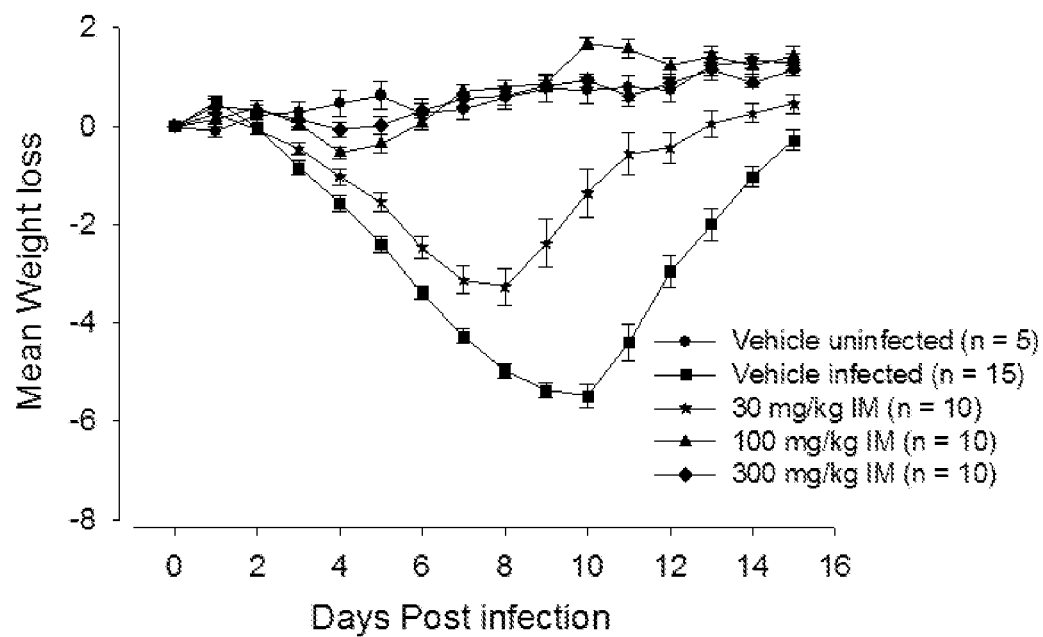
FIG. 6 shows the effect of compound 1 (intramuscular) on weight loss in mice infected with H3N2 A/Victoria/3/75 influenza virus.

FIGS. 2-4 show that compound 1 is phosphorylated but not incorporated into mammalian RNA or DNA. FIG. 2 shows phosphorylation of adenosine in Huh-7 cells. FIG. 3 shows phosphorylation of compound 1 in Huh-7 cells. FIG. 4 shows total RNA and genomic DNA incorporation of compound 1 and adenosine in Huh-7 cells.

Example 7

Effects of Compound 1 (Compound A, Wherein $R_4$ is $NH_2$ and $R_5$ is H) on Replication of Influenza Viruses Materials and Methods
Cells and Virus African green monkey kidney cells (MA-104) were obtained from Whitaker MA Bioproducts, Walkersville, Md., USA). All Vero cells (African green monkey kidney cells, human carcinoma of the larynx cells (A-549), and Madin-Darby canine kidney cells were obtained from the American Type Culture Collection (ATCC, Manassas, Va.). A-549 cells were cultured in Dulbecco's minimal essential medium (DMEM) supplemented with 0.15% $NaHCO_3$ (Hyclone Laboratories, Logan, Utah, USA) and with 10% fetal bovine serum (FBS, Hyclone). The remaining cells were routinely passed in minimal essential medium (MEM with 0.15% $NaHCO_3$; Hyclone Laboratories, Logan, Utah, USA) supplemented with 5% fetal bovine serum (FBS, Hyclone).

When evaluating compounds, the serum was reduced to a final concentration of 2.5%, and gentamicin is added to the test medium to a final concentration of 50 μg/mL. Test medium for influenza assays consisted of MEM without serum, 0.18% $NaHCO_3$, 20 μg trypsin/mL, 2.0 μg EDTA/mL, and 50 μg gentamicin/mL.

For evaluation of toxicity in actively growing cells, cytotoxicity was evaluated by determining the total number of cells as reflected by a NR uptake assay after a 3-day exposure to several concentrations of compound. To quantitate cell growth at 72 h in the presence or absence of drug, plates were seeded with $1 \times 10^3$ MDCK cells, and after 4 h (allowed all cells to attach plate wells) were exposed to selected concentrations of drug in MEM or MEM. After 72 h the plates were treated as described above for the NR assay. Absorbance values were expressed as percent of untreated controls and CC50 values were calculated by regression analysis.

All influenza viruses were obtained from the Centers for Disease Control (Atlanta, Ga.).

Antiviral Testing Procedure

Cytopathic Effect Inhibition Assay (Visual Assay)

Cells were seeded to 96-well flat-bottomed tissue culture plates (Corning Glass Works, Corning, N.Y.), 0.2 mL/well, at the proper cell concentration, and incubated overnight at 37° C. in order to establish a cell monolayer. When the monolayer was established, the growth medium was decanted and the various dilutions of test compound were added to each well (3 wells/dilution, 0.1 mL/well). Compound diluent medium was added to cell and virus control wells (0.1 mL/well). Virus, diluted in test medium, was added to compound test wells (3 wells/dilution of compound) and to virus control wells (6 wells) at 0.1 mL/well. Virus (viral MOI=0.001) was added approximately 5 min after compound. Test medium without virus was added to all toxicity control wells (2 wells/dilution of each test compound) and to cell control wells (6 wells) at 0.1 mL/well. The plates were incubated at 37° C. in a humidified incubator with 5% $CO_2$, 95% air atmosphere until virus control wells had adequate cytopathic effect (CPE) readings (80-100% cell destruction). This was achieved from 4-11 days after virus exposure to cells, depending on the virus. Cells were then examined microscopically for CPE, this being scored from 0 (normal cells) to 4 (maximal, 100%, CPE). The cells in the toxicity control wells were observed microscopically for morphologic changes attributed to cytotoxicity. This cytotoxicity (cell destruction and/or morphology change) was also graded at 100% toxicity, 80% cytotoxicity), 60% cytotoxicity, 40% cytotoxicity, 20% cytotoxicity, and 0 (normal cells). The 50% effective dose (EC50) and 50% cytotoxic dose (IC50) were calculated by regression analysis of the virus CPE data and the toxicity control data, respectively. The selective index (SI) for each compound tested was calculated using the formula: SI=CC50÷EC50.

Neutral Red (NR) Uptake Assay of CPE Inhibition and Compound Cytotoxicity

NR red was chosen as the dye quantitation method for evaluating antiviral drugs based on the findings of Smee et al (supra). This assay was done on the same CPE inhibition test plates described above to verify the inhibitory activity and the cytotoxicity observed by visual observation. The NR assay was performed using a modified method of Cavenaugh et al. (supra) as described by Barnard et al. (supra). Briefly, medium was removed from each well of a plate scored for CPE from a CPE inhibition assay, 0.034% NR was added to each well of the plate and the plate incubated for 2 hr at 37° C. in the dark. The NR solution was then removed from the wells. After rinsing (sometimes cells slough from the plate causing erroneous low up of neutral red) and aspirating to dryness, the remaining dye was extracted for 30 min at room temperature in the dark from the cells using absolute ethanol buffered with Sörenson citrate buffer. Absorbances at 540 nm/405 nm are read with a microplate reader (Opsys MR™, Dynex Technologies, Chantilly, Va., USA). Absorbance values were expressed as percents of untreated controls and EC50, CC50 and SI values were calculated as described above.

Results and Discussion

The influenza viruses were potently inhibited by compound 1 (compound A, wherein $R_4$ is $NH_2$ and $R_5$ is H). EC50 values against the influenza viruses ranged from 0.63-1.8 µg/mL by visual assay and from 1.8-5.6 µg/mL as measured by NR assay (Table 1). All influenza viruses were equivalently susceptible to inhibition by compound 1.

TABLE 1

Effects of a polymerase inhibitor (compound 1) on the replication of various influenza viruses.

| Virus | Visual CPE Assay (µg/mL) | | | Neutral Red Uptake Assay (µg/mL) | | |
|---|---|---|---|---|---|---|
| | EC50 | IC50 | SI | EC50 | IC50 | SI |
| Influenza A H1N1 CA/04/2009 (Pandemic H1N1) | 1.8 | 210 | 120 | 1.8 | 210 | 120 |
| Influenza A H3N2 Brisbane/10/2007 | 1.8 | 260 | 140 | 5.6 | 440 | 79 |
| Influenza A H5N1 VN/1203/2004 Hybrid (on H1N1 backbone) | 0.63 | >1000 | >1600 | 0.99 | 130 | 130 |
| Influenza B Florida | 1.8 | 530 | 290 | 1.8 | 50 | 38 |
| Parainfluenza 3 14702 (MA-104 cells) | 14 | 100 | 7.1 | 10 | 52 | 52 |

Compound 1 was tested against a subset of influenza viral strains and exhibited anti-viral activity against multiple strains (Table 2).

TABLE 2

Antiviral activity of compound 1 in MDCK cells.

| Virus | EC50 (μg/mL) |
|---|---|
| A/CA/04/2009 (Pandemic H1N1) | 1.8 |
| A/Brisbane/10/2007 (H3N2) | 5.6 |
| A/VN/1203/2004 (H5N1) | 0.99 |
| B/Florida | 1.8 |
| A/CA/27/2007 (H1N1) | 0.66 |
| A/NJ/15/2007 (H1N1-H274Y) | 1.39 |
| A/Vic/3/75 (H3N2) | 4.0 |

Example 8

Synergistic Antiviral Activity of Compound 1 (Compound A, Wherein $R_4$ is $NH_2$ and $R_5$ is H) and Neuraminidase Inhibitor in MDCK Cells Madin Darby Canine Kidney (MDCK) cells were infected with influenza virus H3N2 (A/Victoria/3/75) virus and treated with various combinations of compound 1 and peramivir for 72 hrs. Cytopathic effect was determined using neutral red dye uptake assay. The data is shown in table 3.

TABLE 3

Percent Inhibition of Cytopathic Effect in Influenza Infected Cells.

| | Peramivir | | |
|---|---|---|---|
| Compound 1 | 0.0 μM | 0.3 μM | 1.0 μM |
| 0.0 μM | 0 | 3.6 ± 9 | 10.8 ± 11 |
| 1.8 μM | 1.6 ± 6.1 | 22.7 ± 6.1 | 21.5 ± 4.6 |
| 7.8 μM | 25.8 ± 4.8 | 50.4 ± 7.9 | 70.3 ± 4.9 |

The experimental data were evaluated by the three dimensional analysis using Mac Synergy II™ software program (Prichard and Shipman, 1990). The software calculates the theoretical additive interactions from the dose-response curves of the individual drugs. The calculated additive surface, which represents the predicted additive interactions, is then subtracted from the experimental surface to reveal regions of greater (synergy) or less (antagonism)-than-expected interactions. Combination of peramivir and compound 1 in cell culture studies demonstrated a synergistic antiviral effect with a volume of synergy equal to 92 $uM^2$ unit % (FIG. 5).

Example 9

Efficacy of Compound 1 (Compound A, Wherein $R_4$ is $NH_2$ and $R_5$ is H) Intramuscular Injection (IM) in Murine Influenza Model Balb/C mice between 6-8 weeks old were adapted to H3N2 virus (A/Victoria/3/75). Doses of 0, 30, 100, and 300 mg/kg/d qd were given by intramuscular (IM) injection for 5 days starting 1 hr prior to infection. N=50 animals. All animals were followed for 16 days. Endpoints included lethality, mean days to death and weight loss. The effects are shown in FIG. 6.

Compound 1 (IM) in mouse influenza model virus results are also shown in table 4. Compound 1 given IM improves the survival and weight loss in mice infected with influenza virus.

TABLE 4

Compound 1 (IM) in mouse influenza model virus-H3N2 A/Vic/3/75

| Treatment | Dose Level (mg/kg/d) | Survival/ Total | Mean day to death (Mean ± SEM) | Mean weight change (grams ± SEM) Day 8 |
|---|---|---|---|---|
| Vehicle, uninfected | 0 | 3/3 | >16 | 0.58 ± 0.23 |
| Vehicle, infected | 0 | 7/15 | 10.3 ± 0.3 | −4.98 ± 0.14 |

TABLE 4-continued

Compound 1 (IM) in mouse influenza model virus-H3N2 A/Vic/3/75

| Treatment | Dose Level (mg/kg/d) | Survival/ Total | Mean day to death (Mean ± SEM) | Mean weight change (grams ± SEM) Day 8 |
|---|---|---|---|---|
| compound 1 | 30 | 10/10* | >16 | −3.27 ± 0.37** |
| compound 1 | 100 | 10/10* | >16 | 0.78 ± 0.17** |
| compound 1 | 300 | 10/10* | >16 | 0.60 ± 0.17** |

*P < 0.001 compared to vehicle infected group (log rank test)
**P < 0.001 compared to vehicle infected group (t-test)

Example 10

Figure 7:
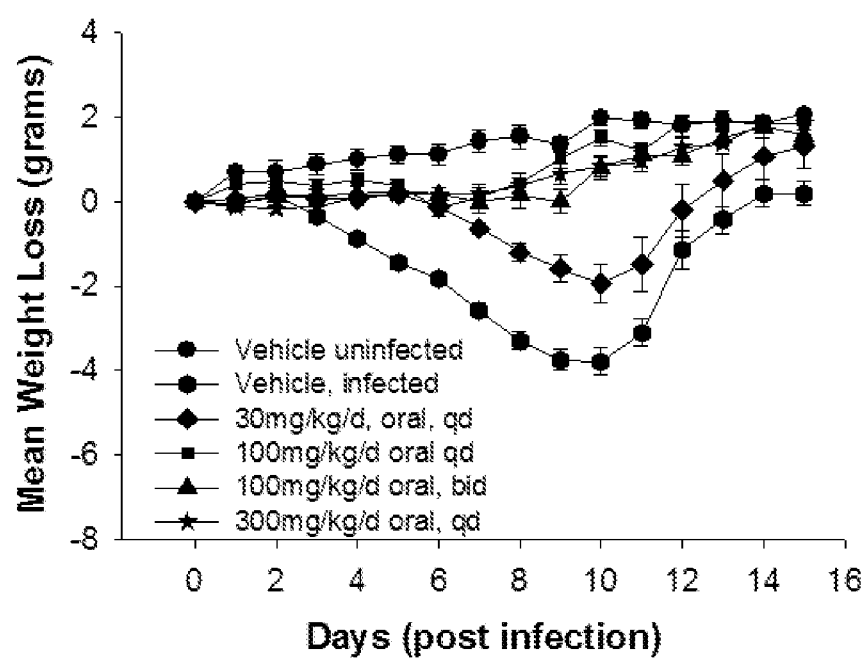
FIG. 7 shows the effect of compound 1 (oral) on weight loss in mice infected with H3N2 A/Victoria/3/75 influenza virus.

Efficacy of Compound 1 (Compound A, Wherein $R_4$ is $NH_2$ and $R_5$ is H) Oral Administration in Murine Influenza Model Balb/C mice between 6-8 weeks old were adapted to H3N2 virus (A/Victoria/3/75). Doses of 0, 30, 100, and 300 mg/kg/d qd and 100 mg/kg/d bid were given orally. N=60 animals. All animals were followed for 16 days. Endpoints included lethality, mean days to death and weight loss. The effects of orally administered compound 1 on weight loss in mice infected with H3N2 A/Vic/3/75 influenza virus are shown in FIG. 7.

Oral administration of compound 1 in mouse influenza model virus results are also shown in table 5. Compound 1 given orally improves the survival and weight loss in mice infected with influenza virus.

TABLE 5

Compound 1 (Oral) in mouse influenza model virus-H3N2 A/Vic/3/75

| Treatment | Dose Level (mg/kg/d) qd | Survival/ Total | Mean day to death (Mean ± SEM) | Mean weight change (grams ± SEM) Day 9 |
|---|---|---|---|---|
| Vehicle, uninfected | 0 | 3/3 | >16 | 1.36 ± 0.96 |
| Vehicle, infected | 0 | 7/15 | 10.5 ± 0.3 | −3.74 ± 0.23 |
| compound 1 | 30 | 10/10* | >16 | −1.58 ± 0.32** |
| compound 1 | 100 | 10/10* | >16 | 1.03 ± 0.22** |
| compound 1 | 100 (bid) | 10/10* | >16 | 0.01 ± 0.27** |
| compound 1 | 300 | 10/10* | >16 | 0.66 ± 0.23** |

*P < 0.001 compared to vehicle infected group (log rank test)
**P < 0.001 compared to vehicle infected group (t-test)

Example 11

Pharmacokinetic Studies in Mice

Female Balb/c mice (N=30) were dosed orally with compound 1 at 100 mg/kg. Mice were bled through the retro orbital sinus at t=0.17, 0.5, 1.0, 3, 6, and 24 hrs (5 mice each per time point), centrifuged and plasma was stored at −80° C. Plasma drug levels were measured via LC/MS/MS analysis.

Mouse plasma levels for compound 1 (compound A, wherein $R_4$ is $NH_2$ and $R_5$ is H) after oral administration are shown in table 6.

TABLE 6

Compound 1 (Oral) in mouse influenza model virus-H3N2 A/Vic/3/75

| Timepoint (hr) | Plasma drug levels (ng/mL) (Mean ± SEM) |
|---|---|
| 0.17 | 607.1 ± 61.0 |
| 0.5 | 910.0 ± 121.9 |
| 1 | 341.6 ± 121.9 |
| 3 | 89.7 ± 8.5 |
| 5 | 94.2 ± 6.4 |
| 24 | 50.5 ± 8.9 |

Example 12

Synthesis of Compound (3R,4R,5S)-4-acetamido-5-((tert-butoxycarbonyl)amino)-3-(pentan-3-yloxy) cyclohex-1-enecarboxylic acid (9-3)

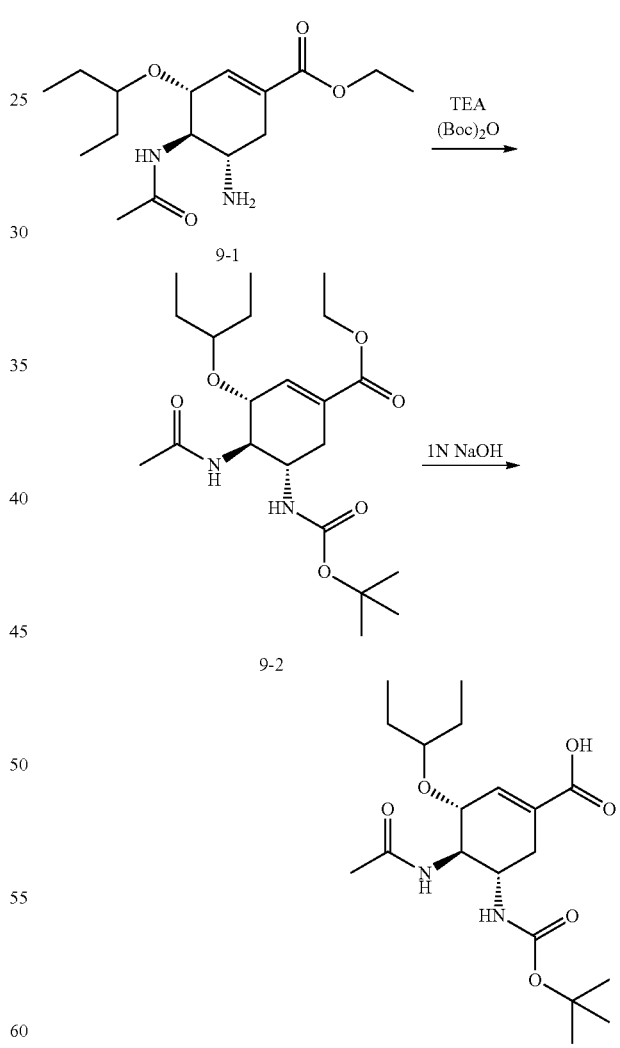

Step-1

To a solution of (3R,4R,5S)-ethyl 4-acetamido-5-amino-3-(pentan-3-yloxy)cyclohex-1-enecarboxylate (9-1) (Oseltamivir phosphate, 2.5 g, 6.09 mmol) in water (20 mL) and methanol (20 mL) was added triethylamine (2.46 mL, 17.67 mmol) at room temperature followed by di-tert-butyl carbonate (Boc anhydride, 2.87 g, 16.45 mmol). The reaction mixture was stirred at room temperature overnight. The solid product obtained was collected by filtration, washed with water, dried under vacuum to furnish (3R,4R,5S)-ethyl 4-acetamido-5-((tert-butoxycarbonyl)amino)-3-(pentan-3-yloxy)cyclohex-1-enecarboxylate (9-2) (1.95 g, 4.73 mmol, 78% yield) as a white solid; $^1$HNMR (300 MHz, DMSO-$d_6$) δ 7.79 (d, J=9.0 Hz, 1H), 6.61 (d, J=8.9 Hz, 2H), 4.22-4.03 (m, 3H), 3.76-3.49 (m, 2H), 3.39 (p, J=5.5 Hz, 1H), 2.45 (d, J=5.0 Hz, 1H), 2.24 (dd, J=17.7, 10.0 Hz, 1H), 1.78 (s, 3H), 1.47-1.31 (m, 13H), 1.22 (t, J=7.1 Hz, 3H), 0.80 (dt, J=19.7, 7.3 Hz, 6H); MS (ES+) 413.22 (M+1, 435.20 (M+Na), 847.44 (2M+Na); (ES−) 410.64 (M−1), 446.71 (M+Cl); Elemental analysis calculated for $C_{21}H_{36}N_2O_6$: C, 61.14; H, 8.80; N, 6.79. Found: C, 61.11; H, 8.90; N, 6.75.

Step-2

To a solution of (3R,4R,5S)-ethyl 4-acetamido-5-((tert-butoxycarbonyl)amino)-3-(pentan-3-yloxy)cyclohex-1-enecarboxylate (9-2) (1 g, 2.42 mmol) in Tetrahydrofuran (5 mL) and MeOH (5 mL) was added 1 N sodium hydroxide (4.85 mL, 4.85 mmol). The reaction mixture was stirred at room temperature for 2 h and concentrated in vacuum to remove organic solvents. The aqueous layer was acidified with acetic acid and the solid obtained was collected by filtration, washed with water, dried under vacuum overnight to furnish (3R,4R,5S)-4-acetamido-5-((tert-butoxycarbonyl)amino)-3-(pentan-3-yloxy)cyclohex-1-enecarboxylic acid (9-3) (823 mg, 2.14 mmol, 88% yield) as a white solid.

$^1$HNMR (300 MHz, DMSO-$d_6$) δ 12.56 (s, 1H), 7.79 (d, J=9.0 Hz, 1H), 6.70-6.45 (m, 2H), 4.05 (d, J=8.5 Hz, 1H), 3.68 (m, 1H), 3.55 (m, 1H), 3.42-3.35 (m, 1H), 2.42 (d, J=4.7 Hz, 1H), 2.20 (m, 1H), 1.78 (s, 3H), 1.51-1.38 (m, 4H), 1.37 (s, 9H), 0.80 (m, 6H); MS (ES+) 407.2 (M+Na), 791.4 (2M+Na); (ES−) 767.5 (2M−1). Elemental analysis calculated for $C_{19}H_{32}N_2O_6$: C, 59.36; H, 8.39; N, 7.29. Found: C, 59.32; H, 8.55; N, 7.35.

Example 13

Synthesis of Compound (3R,4R,5S)-((2R,3R,4S,5S)-5-(4-amino-5H-pyrrolo[3,2-d]pyrimidin-7-yl)-3,4-dihydroxypyrrolidin-2-yl)methyl 4-acetamido-5-amino-3-(pentan-3-yloxy)cyclohex-1-enecarboxylate (10-3)

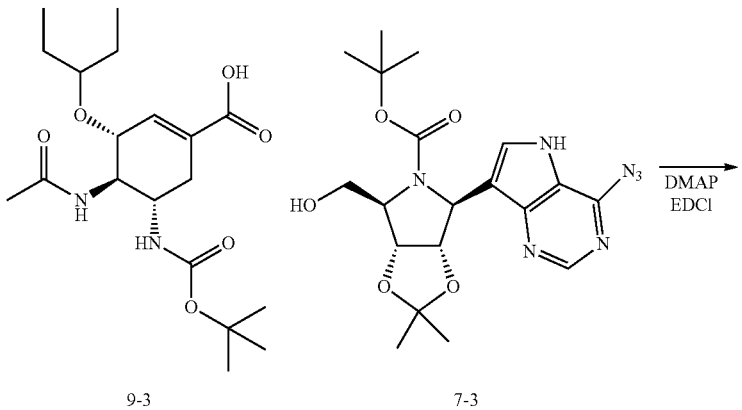

9-3            7-3

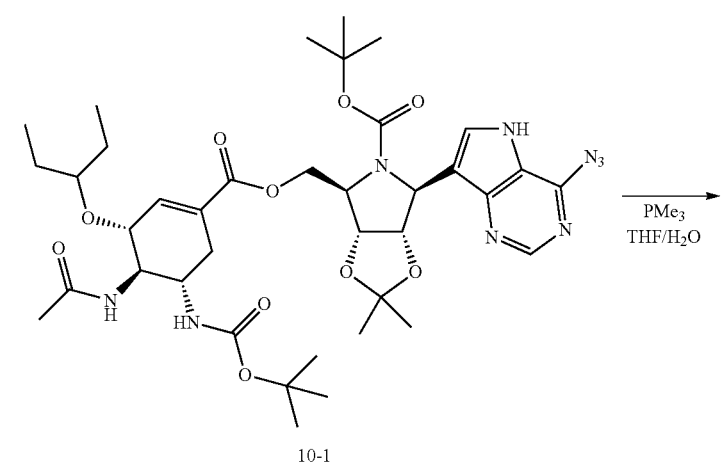

10-1

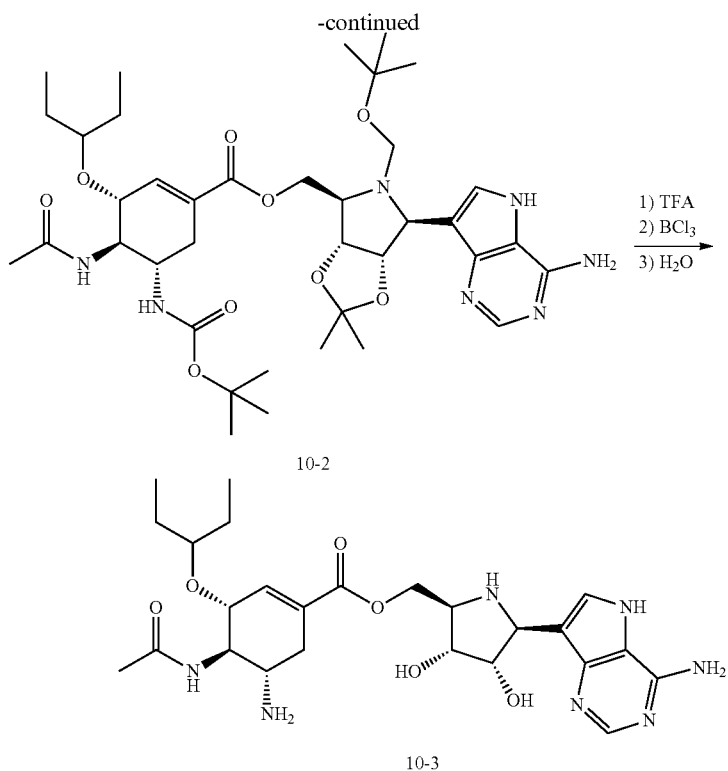

10-2

10-3

Step-1

To the solution of (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (7-3) (0.86 g, 2.0 mmol) and (3R,4R,5S)-4-acetamido-5-(tert-butoxycarbonylamino)-3-(pentan-3-yloxy)cyclohex-1-enecarboxylic acid (9-3) (0.77 g, 2.0 mmol) in CH$_2$Cl$_2$ (20 mL) was added 1-(3-dimethylaminopropyl)-3-ethylcarbodiimide hydrochloride (0.96 g, 5.0 mmol) and N,N-dimethylpyridin-4-amine (0.073 g, 0.6 mmol). The reaction mixture was stirred at room temperature for 5 days and quenched with water. The organic layer was separated washed with brine, dried and concentrated in vacuum. The residue obtained was purified twice by flash column chromatography (silica gel 40 g, eluting with ethyl acetate in hexane 0-100%) to furnish (3aR,4R,6S,6aS)-tert-butyl 4-((((3R,4R,5S)-4-acetamido-5-((isopropoxycarbonyl)amino)-3-(pentan-3-yloxy)cyclohex-1-enecarbonyl)oxy)methyl)-6-(4-azido-5H-pyrrolo[3,2-d]pyrimidin-7-yl)-2,2-dimethyldihydro-3aH-[1,3]dioxolo[4,5-c]pyrrole-5(4H)-carboxylate (10-1) (0.65 g, 61%) that was contaminated with (3aS,4S,6R,6aR)-tert-butyl 4-(4-azido-5H-pyrrolo[3,2-d]pyrimidin-7-yl)-6-(hydroxymethyl)-2,2-dimethyldihydro-3aH-[1,3]dioxolo[4,5-c]pyrrole-5(4H)-carboxylate (7-3). The product was taken as such to next step. MS (ES+) 820.2 (M+Na); (ES−) 796.8 (M−1).

Step-2

To a solution of (3aR,4R,6S,6a5)-tert-butyl 4-((((3R,4R,5S)-4-acetamido-5-((isopropoxycarbonyl)amino)-3-(pentan-3-yloxy)cyclohex-1-enecarbonyl)oxy)methyl)-6-(4-azido-5H-pyrrolo[3,2-d]pyrimidin-7-yl)-2,2-dimethyldihydro-3aH-[1,3]dioxolo[4,5-c]pyrrole-5(4H)-carboxylate (10-1) (500 mg, 0.6 mmol) in THF (20 mL) and water (1 mL) was added PMe$_3$ (6 mL, 1 M in THF), stirred at room temperature for 5 h and concentrated in vacuum to dryness. The residue obtained was purified twice by flash column chromatography (silica gel 24 gm, eluting with 0-100% ethyl acetate in hexane) to give (3 aR,4R,6S,6aS)-tert-butyl 4-((((3R,4R,5S)-4-acetamido-5-((tert-butoxycarbonyl)amino)-3-(pentan-3-yloxy)cyclohex-1-enecarbonyl)oxy)methyl)-6-(4-amino-5H-pyrrolo[3,2-d]pyrimidin-7-yl)-2,2-dimethyldihydro-3aH-[1,3]dioxolo[4,5-c]pyrrole-5 (4H)-carboxylate (10-2) (320 mg, 69%) as a white solid.

$^1$HNMR (300 MHz, DMSO) δ 10.88 (s, 1H), 8.10 (s, 1H), 7.79 (d, J=9.1 Hz, 1H), 7.33 (s, 1H), 6.77 (s, 2H), 6.68 (s, 1H), 6.60 (s, 1H), 5.26 (d, J=4.8 Hz, 1H), 5.18 (d, J=17.2 Hz, 1H), 4.89 (d, J=6.0 Hz, 1H), 4.21 (br, 2H), 4.14-4.01 (m, 2H), 3.79-3.49 (m, 2H), 3.46-3.34 (m, 1H), 2.27 (m, 1H), 1.78 (s, 3H), 1.42 (s, 3H), 1.37 (d, J=1.5 Hz, 22H), 1.28 (s, 3H), 0.83 (t, J=7.4 Hz, 3H), 0.77 (t, J=7.3 Hz, 3H); MS (ES+) 772.3 (M+1); (ES−) 769.7 (M−1); Elemental analysis calculated for C$_{38}$H$_{57}$N$_7$O$_{10}$.1.5H$_2$O: C, 57.13; H, 7.57; N, 12.27. Found: C, 56.89; H, 7.54; N, 11.98.

Step-3

A solution of (3aR,4R,6S,6aS)-tert-butyl 4-((((3R,4R,5S)-4-acetamido-5-((tert-butoxycarbonyl)amino)-3-(pentan-3-yloxy)cyclohex-1-enecarbonyl)oxy)methyl)-6-(4-amino-5H-pyrrolo[3,2-d]pyrimidin-7-yl)-2,2-dimethyldihydro-3aH-[1,3]dioxolo[4,5-c]pyrrole-5(4H)-carboxylate (10-2) (300 mg, 0.39 mmol) in TFA (10 mL) was stirred at room temperature for 1 h and concentrated in vacuum to dryness. The residue obtained was dissolved in AcOH (10 mL) and added BCl$_3$ (2 mL, 1 M in DCM). The reaction mixture was stirred at room temperature for 4 min and quenched with water (5 mL). The reaction mixture was concentrated in vacuum to dryness and residue obtained was freeze-dried to afford product (10-3) (288 mg, 74%) as a white solid. The product (10-3) (200 mg) was dissolved in 3 mL of water and dialyzed with Spectrum Cellulose Ester Dialysis Membrane (MWCO: 100-500D), and then freeze-dried to give 125 mg of (3R,4R,5S)-((2R,3R,4S,5S)-5-(4-amino-5H-pyrrolo[3,2-d]pyrimidin-7-yl)-3,4-dihydroxypyrrolidin-2-yl)methyl 4-acetamido-5-amino-3-(pentan-3-yloxy)cyclohex-1-enecarboxylate (10-3) as a white solid;

$^{1}$H NMR (300 MHz, D$_2$O) δ 8.24 (d, J=4.8 Hz, 1H), 7.77 (s, 1H), 6.62 (s, 1H), 4.86 (d, J=7.4 Hz, 1H), 4.63-4.53 (m, 2H), 4.50-4.41 (m, 2H), 4.19 (d, J=9.2 Hz, 1H), 4.00-3.87 (m, 2H), 3.51 (td, J=10.8, 5.7 Hz, 1H), 3.39-3.29 (m, 1H), 2.87 (dd, J=17.1, 5.7 Hz, 1H), 2.49-2.30 (m, 1H), 2.00 (s, 3H), 1.47-1.25 (m, 4H), 0.73 (t, J=7.4 Hz, 3H), 0.60 (t, J=7.4 Hz, 3H); MS (ES+) 532.1 (M+1). Elemental analysis calculated for C$_{25}$H$_{37}$N$_7$O$_6$·3HCl·2H$_2$O: C, 44.35; H, 6.55; N, 14.48. Found: C, 44.03; H, 6.72; N, 14.28.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

The invention claimed is:
1. A compound of formula I:

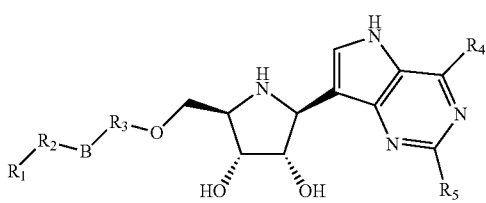

(I)

wherein
$R_1$ is selected from

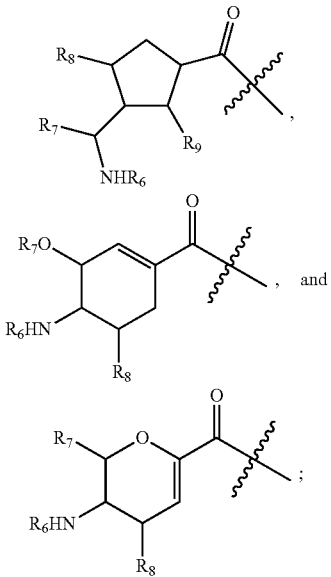

$R_2$ is a bond, O, or S;
$R_3$ is a bond, C(=O), C(=S), C(=NR$_{10}$), OC(=O), OC(=S), OC(=NR$_{10}$), N(R$_{11}$)C(=O), N(R$_{11}$)C(=S), or N(R$_{11}$)C(=NR$_{10}$);

$R_4$ is OH or N(R$_{15}$)$_2$;

$R_5$ is H or N(R$_{15}$)$_2$;

$R_6$ is $R_{11}$, C(=O)—R$_{11}$, or SO$_2$—R$_{11}$;

$R_7$ is H or $R_{12}$, wherein $R_{12}$ is optionally substituted with one or more groups selected from lower alkyl, OR$_{11}$, O—C(=O)—R$_{11}$, O—C(=O)O—R$_{11}$, O—C(=O)N(R$_{11}$)$_2$, O—C(=S)—R$_{11}$, O—C(=S)O—R$_{11}$, and O—C(=S)N(R$_{11}$)$_2$;

$R_8$ is OR$_{11}$, O—C(=O)—R$_{11}$, O—C(=O)O—R$_{11}$, O—C(=O)N(R$_{11}$)$_2$, O—C(=S)—R$_{11}$, O—C(=S)O—R$_{11}$, O—C(=S)N(R$_{11}$)$_2$, N(R$_{11}$)$_2$, N(R$_{11}$)C(=O)—R$_{11}$, N(R$_{11}$)C(=O)O(R$_{11}$)$_2$, N(R$_{11}$)C(=O)N(R$_{11}$)$_2$, N(R$_{11}$)C(=S)—R$_{11}$, N(R$_{11}$)C(=S)O—R$_{11}$, N(R$_{11}$)C(=S)N(R$_{11}$)$_2$, or N(R$_{11}$)C(=NR$_{10}$)N(R$_{11}$)$_2$;

$R_9$ is H, OH, O—C(=O)O—R$_{11}$, O—C(=O)N(R$_{11}$)$_2$, O—C(=S)—R$_{11}$, O—C(=S)O—R$_{11}$, O—C(=S)N(R$_{11}$)$_2$;

B is a bond, R$_{12}$, R$_{12}$—R$_{13}$, R$_{12}$—R$_{13}$—R$_{14}$, R$_{12}$—O—R$_{13}$, R$_{12}$—S—R$_{13}$, R$_{12}$—N(R$_{11}$)$_2$—R$_{13}$, R$_{12}$—C(=O)—R$_{13}$, R$_{12}$—C(=S)—R$_{13}$, R$_{12}$—C(=NR$_{10}$)—R$_{13}$, R$_{12}$—OC(=O)—R$_{13}$, R$_{12}$—OC(=S)—R$_{13}$, R$_{12}$—OC(=NR$_{10}$)—R$_{13}$, R$_{12}$—SC(=O)—R$_{13}$, R$_{12}$—SC(=S)—R$_{13}$, R$_{12}$—SC(=NR$_{10}$)—R$_{13}$, R$_{12}$—N(R$_{11}$)C(=O)—R$_{13}$, R$_{12}$—N(R$_{11}$)C(=S)—R$_{13}$, R$_{12}$—N(R$_{11}$)C(=NR$_{10}$)—R$_{13}$, R$_{12}$—OC(=O)—OR$_{13}$, R$_{12}$—OC(=S)—OR$_{13}$, R$_{12}$—OC(=NR$_{10}$)—OR$_{13}$, R$_{12}$—OC(=O)—N(R$_{11}$)R$_{13}$, R$_{12}$—OC(=S)—N(R$_{11}$)R$_{13}$, R$_{12}$—OC(=NR$_{10}$)—N(R$_{11}$)R$_{13}$, R$_{12}$—OC(=O)—SR$_{13}$, R$_{12}$—OC(=S)—SR$_{13}$, R$_{12}$—OC(=NR$_{10}$)—SR$_{13}$, R$_{12}$—N(R$_{11}$)C(=O)—OR$_{13}$, R$_{12}$—N(R$_{11}$)C(=S)—OR$_{13}$, R$_{12}$—N(R$_{11}$)C(=NR$_{10}$)—OR$_{13}$, R$_{12}$—N(R$_{11}$)C(=O)—N(R$_{11}$)R$_{13}$, R$_{12}$—N(R$_{11}$)C(=S)—N(R$_{11}$)R$_{13}$, R$_{12}$—N(R$_{11}$)C(=NR$_{10}$)—N(R$_{11}$)R$_{13}$, R$_{12}$—N(R$_{11}$)C(=O)—SR$_{13}$, R$_{12}$—N(R$_{11}$)C(=S)—SR$_{13}$, R$_{12}$—N(R$_{11}$)C(=NR$_{10}$)—SR$_{13}$, R$_{12}$—SC(=O)—OR$_{13}$, R$_{12}$—SC(=S)—OR$_{13}$, R$_{12}$—SC(=NR$_{10}$)—OR$_{13}$, R$_{12}$—SC(=O)—SR$_{13}$, R$_{12}$—SC(=S)—SR$_{13}$, R$_{12}$—SC(=NR$_{10}$)—SR$_{13}$, R$_{12}$—SC(=O)—N(R$_{11}$)R$_{13}$, R$_{12}$—SC(=S)—N(R$_{11}$)R$_{13}$, or R$_{12}$—SC(=NR$_{10}$)—N(R$_{11}$)R$_{13}$; wherein each R$_{12}$, R$_{13}$, and R$_{14}$ are optionally substituted with one or more R$_{15}$;

$R_{10}$ is independently H, lower alkyl, lower alkenyl, lower alkynyl, lower cycloalkyl, aryl, heteroaryl, OR$_{11}$, or N(R$_{11}$)$_2$;

$R_{11}$ is independently H, lower alkyl, lower alkenyl, lower alkynyl, lower cycloalkyl, aryl, or heteroaryl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently halogen, R$_{10}$, OC(=O)R$_{11}$, OC(=S)R$_{11}$, OC(=NR$_{10}$)R$_{11}$, OC(=O)OR$_{11}$, OC(=S)OR$_{11}$, OC(=NR$_{10}$)OR$_{11}$, OC(=O)N(R$_{11}$)$_2$, OC(=S)N(R$_{11}$)$_2$, OC(=NR$_{10}$)N(R$_{11}$)$_2$, N(R$_{11}$)C(=O)R$_{11}$, N(R$_{11}$)C(=S)R$_{11}$, N(R$_{11}$)C(=NR$_{10}$)R$_{11}$, N(R$_{11}$)C(=O)OR$_{11}$, N(R$_{11}$)C(=S)OR$_{11}$, N(R$_{11}$)C(=NR$_{10}$)OR$_{11}$, N(R$_{11}$)C(=O)N(R$_{11}$)$_2$, N(R$_{11}$)C(=S)N(R$_{11}$)$_2$, or N(R$_{11}$)C(=NR$_{10}$)N(R$_{11}$)$_2$;

or a pharmaceutically acceptable salt thereof.

2. The compound of claim 1, wherein $R_1$ is selected from the group consisting of

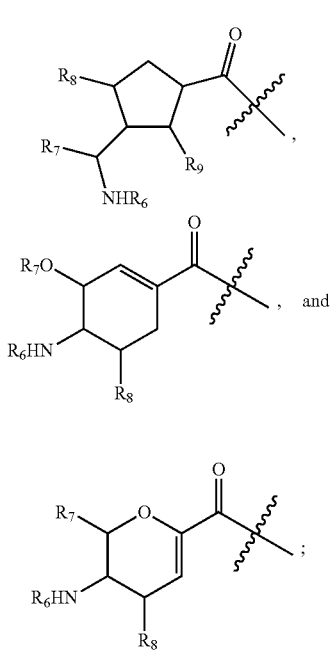

$R_2$ is a bond, O, or S;
$R_3$ is a bond, C(=O), C(=S), or N($R_{11}$)C(=O);
$R_4$ is OH or $NH_2$;
$R_5$ is H or $NH_2$;
$R_6$ is C(=O)—$R_{11}$;
$R_7$ is lower alkyl, optionally substituted with one or more groups selected from lower alkyl, $OR_{11}$, O—C(=O)—$R_{11}$, O—C(=O)O—$R_{11}$, and O—C(=O)N($R_{11}$)$_2$;
$R_8$ is $OR_{11}$, O—C(=O)—$R_{11}$, O—C(=O)O—$R_{11}$, O—C(=O)N($R_{11}$)$_2$, N($R_{11}$)$_2$, N(H)C(=O)O($R_{11}$)$_2$, or N(H)C(=NH)$NH_2$;
$R_9$ is H, OH, O—C(=O)O—$R_{11}$, or O—C(=O)N($R_{11}$)$_2$;
B is a bond, $R_{12}$, $R_{12}$—$R_{13}$, $R_{12}$—O—$R_{13}$; $R_{12}$—OC(=O)—$R_{13}$, $R_{12}$—N($R_{11}$)C(=O)—$R_{13}$, $R_{12}$—OC(=O)—$OR_{13}$, $R_{12}$—OC(=O)—N($R_{11}$)$R_{13}$, $R_{12}$—N($R_{11}$)C(=O)—$OR_{13}$, or $R_{12}$—N($R_{11}$)C(=O)—N($R_{11}$)$R_{13}$; wherein each $R_{12}$, $R_{13}$, and $R_{14}$ are optionally substituted with one or more $R_{15}$;
$R_{10}$ is independently H, lower alkyl, lower alkenyl, lower alkynyl, lower cycloalkyl, aryl, heteroaryl, $OR_{11}$, or N($R_{11}$)$_2$;
$R_{11}$ is independently H, or lower alkyl optionally substituted with one or more lower alkyl;
$R_{12}$ is independently lower alkyl, lower alkenyl, lower alkynyl, lower cycloalkyl, aryl, or heteroaryl;
$R_{13}$ is independently lower alkyl, lower alkenyl, lower alkynyl, lower cycloalkyl, aryl, or heteroaryl;
$R_{14}$ is independently lower alkyl, lower alkenyl, lower alkynyl, lower cycloalkyl, aryl, or heteroaryl; and
$R_{15}$ is independently $R_{10}$, N($R_{11}$)C(=O)$R_{11}$, or N($R_{11}$)C(=O)O$R_{11}$;
or a pharmaceutically acceptable salt thereof.

3. The compound of claim 1, wherein $R_1$ is

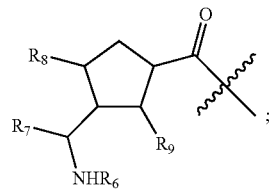

$R_2$ is a bond or O;
$R_3$ is a bond or C(=O);
$R_4$ is $NH_2$;
$R_5$ is hydrogen;
$R_6$ is C(=O)—$CH_3$;
$R_7$ is —CH($CH_2CH_3$)$_2$;
$R_8$ is N(H)C(=NH)$NH_2$;
$R_9$ is OH;
B is a bond, lower alkyl, lower alkyl-OC(=O)—$R_{13}$; wherein $R_{13}$ is optionally substituted with $R_{15}$;
$R_{11}$ is independently H, or lower alkyl;
$R_{13}$ is lower alkyl; and
$R_{15}$ is lower alkyl, N($R_{11}$)$_2$, or N(H)C(=O)$R_{11}$;
or a pharmaceutically acceptable salt thereof.

4. The compound of claim 1, wherein $R_1$ is

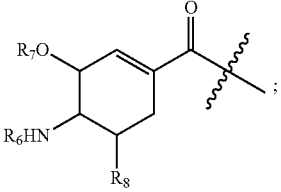

$R_2$ is a bond or O;
$R_3$ is a bond or C(=O);
$R_4$ is $NH_2$;
$R_5$ is hydrogen;
$R_6$ is C(=O)—$CH_3$;
$R_7$ is —CH($CH_2CH_3$)$_2$;
$R_8$ is $NH_2$;
B is a bond, lower alkyl, lower alkyl-OC(=O)—$R_{13}$; wherein $R_{13}$ is optionally substituted with $R_{15}$;
$R_{11}$ is independently H, or lower alkyl;
$R_{13}$ is lower alkyl; and
$R_{15}$ is lower alkyl, N($R_{11}$)$_2$, or N(H)C(=O)$R_{11}$;
or a pharmaceutically acceptable salt thereof.

5. The compound of claim 1, wherein $R_1$ is

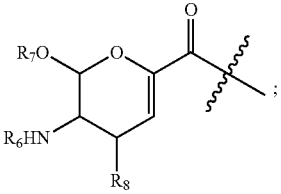

$R_2$ is a bond, or O;
$R_3$ is a bond or C(=O);
$R_4$ is $NH_2$;
$R_5$ is hydrogen;
$R_6$ is C(=O)—$CH_3$;
$R_7$ is 1,2,3-trihydroxypropyl;

R₈ is NH₂C(=NH)NH₂;
B is a bond, lower alkyl, lower alkyl-OC(=O)—R₁₃; wherein R₁₃ is optionally substituted with R₁₅;
R₁₁ is independently H, or lower alkyl;
R₁₃ is lower alkyl; and
R₁₅ is lower alkyl, N(R₁₁)₂, or N(H)C(=O)R₁₁;
or a pharmaceutically acceptable salt thereof.

6. The compound of claim 1, wherein the compound is

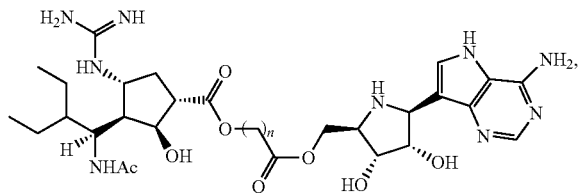

wherein n is an integer from 1 to 6; or a pharmaceutically acceptable salt thereof.

7. The compound of claim 1, wherein the compound is

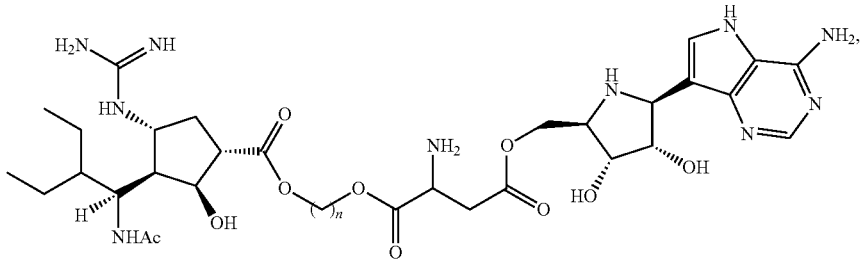

wherein n is an integer from 1 to 6; or a pharmaceutically acceptable salt thereof.

8. The compound of claim 1, wherein the compound is

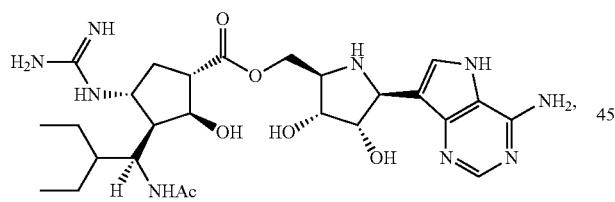

or a pharmaceutically acceptable salt thereof.

9. A method for inhibiting, treating or suppressing a viral infection, comprising administering to a subject in need thereof an effective amount of a compound of formula I:

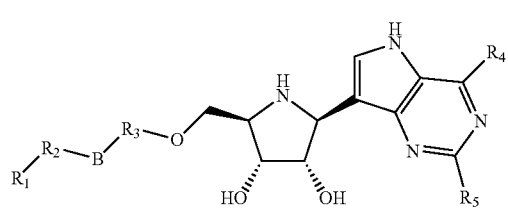

wherein

R₁ is selected from

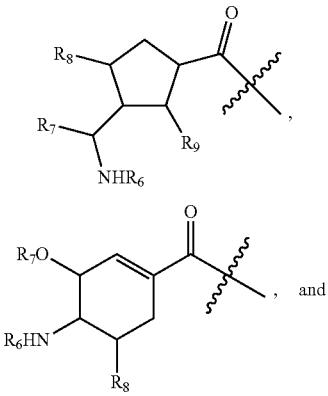

-continued

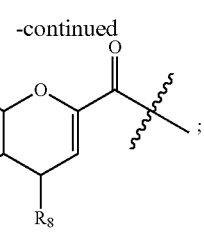

R₂ is a bond, O, or S;
R₃ is a bond, C(=O), C(=S), C(=NR₁₀), OC(=O), OC(=S), OC(=NR₁₀), N(R₁₁)C(=O), N(R₁₁)C(=S), or N(R₁₁)C(=NR₁₀);
R₄ is OH or N(R₁₅)₂;
R₅ is H or N(R₁₅)₂;
R₆ is R₁₁, C(=O)—R₁₁, or SO₂—R₁₁;
R₇ is H or R₁₂, wherein R₁₂ is optionally substituted with one or more groups selected from lower alkyl, OR₁₁, O—C(=O)—R₁₁, O—C(=O)O—R₁₁, O—C(=O)N(R₁₁)₂, O—C(=S)—R₁₁, O—C(=S)O—R₁₁, and O—C(=S)N(R₁₁)₂;
R₈ is OR₁₁, O—C(=O)—R₁₁, O—C(=O)O—R₁₁, O—C(=O)N(R₁₁)₂, O—C(=S)—R₁₁, O—C(=S)O—R₁₁, O—C(=S)N(R₁₁)₂, N(R₁₁)₂, N(R₁₁)C(=O)—R₁₁, N(R₁₁)C(=O)O(R₁₁)₂, N(R₁₁)C(=O)N(R₁₁)₂, N(R₁₁)C(=S)—R₁₁, N(R₁₁)C(=S)O—R₁₁, N(R₁₁)C(=S)N(R₁₁)₂, or N(R₁₁)C(=NR₁₀)N(R₁₁)₂;
R₉ is H, OH, O—C(=O)O—R₁₁, O—C(=O)N(R₁₁)₂, O—C(=S)—R₁₁, O—C(=S)O—R₁₁, O—C(=S)N(R₁₁)₂;

B is a bond, $R_{12}$, $R_{12}$—$R_{13}$, $R_{12}$—$R_{13}$—$R_{14}$, $R_{12}$—O—$R_{13}$, $R_{12}$—S—$R_{13}$, $R_{12}$—N($R_{11}$)$_2$—$R_{13}$, $R_{12}$—C(=O)—$R_{13}$, $R_{12}$—C(=S)—$R_{13}$, $R_{12}$—C(=NR$_{10}$)—$R_{13}$, $R_{12}$—OC(=O)—$R_{13}$, $R_{12}$—OC(=S)—$R_{13}$, $R_{12}$—OC(=NR$_{10}$)—$R_{13}$, $R_{12}$—SC(=O)—$R_{13}$, $R_{12}$—SC(=S)—$R_{13}$, $R_{12}$—SC(=NR$_{10}$)—$R_{13}$, $R_{12}$—N($R_{11}$)C(=O)—$R_{13}$, $R_{12}$—N($R_{11}$)C(=S)—$R_{13}$, $R_{12}$—N($R_{11}$)C(=NR$_{10}$)—$R_{13}$, $R_{12}$—OC(=O)—O$R_{13}$, $R_{12}$—OC(=S)—O$R_{13}$, $R_{12}$—OC(=NR$_{10}$)—O$R_{13}$, $R_{12}$—OC(=O)—N($R_{11}$)$R_{13}$, $R_{12}$—OC(=S)—N($R_{11}$)$R_{13}$, $R_{12}$—OC(=NR$_{10}$)—N($R_{11}$)$R_{13}$, $R_{12}$—OC(=O)—S$R_{13}$, $R_{12}$—OC(=S)—S$R_{13}$, $R_{12}$—OC(=NR$_{10}$)—S$R_{13}$, $R_{12}$—N($R_{11}$)C(=O)—O$R_{13}$, $R_{12}$—N($R_{11}$)C(=S)—O$R_{13}$, $R_{12}$—N($R_{11}$)C(=NR$_{10}$)—O$R_{13}$, $R_{12}$—N($R_{11}$)C(=O)—N($R_{11}$)$R_{13}$, $R_{12}$—N($R_{11}$)C(=S)—N($R_{11}$)$R_{13}$, $R_{12}$—N($R_{11}$)C(=NR$_{10}$)—N($R_{11}$)$R_{13}$, $R_{12}$—N($R_{11}$)C(=O)—S$R_{13}$, $R_{12}$—N($R_{11}$)C(=S)—S$R_{13}$, $R_{12}$—N($R_{11}$)C(=NR$_{10}$)—S$R_{13}$, $R_{12}$—SC(=O)—O$R_{13}$, $R_{12}$—SC(=S)—O$R_{13}$, $R_{12}$—SC(=NR$_{10}$)—O$R_{13}$, $R_{12}$—SC(=O)—S$R_{13}$, $R_{12}$—SC(=S)—S$R_{13}$, $R_{12}$—SC(=NR$_{10}$)—S$R_{13}$, $R_{12}$—SC(=O)—N($R_{11}$)$R_{13}$, $R_{12}$—SC(=S)—N($R_{11}$)$R_{13}$, or $R_{12}$—SC(=NR$_{10}$)—N($R_{11}$)$R_{13}$; wherein each $R_{12}$, $R_{13}$, and $R_{14}$ are optionally substituted with one or more $R_{15}$;

$R_{10}$ is independently H, lower alkyl, lower alkenyl, lower alkynyl, lower cycloalkyl, aryl, heteroaryl, O$R_{11}$, or N($R_{11}$)$_2$;

$R_{11}$ is independently H, lower alkyl, lower alkenyl, lower alkynyl, lower cycloalkyl, aryl, or heteroaryl;

$R_{12}$ is independently lower alkyl, lower alkenyl, lower alkynyl, lower cycloalkyl, aryl, or heteroaryl;

$R_{13}$ is independently lower alkyl, lower alkenyl, lower alkynyl, lower cycloalkyl, aryl, or heteroaryl;

$R_{14}$ is independently lower alkyl, lower alkenyl, lower alkynyl, lower cycloalkyl, aryl, or heteroaryl; and $R_{15}$ is independently halogen, $R_{10}$, OC(=O)$R_{11}$, OC(=S)$R_{11}$, OC(=NR$_{10}$)$R_{11}$, OC(=O)O$R_{11}$, OC(=S)O$R_{11}$, OC(=NR$_{10}$)O$R_{11}$, OC(=O)N($R_{11}$)$_2$, OC(=S)N($R_{11}$)$_2$, OC(=NR$_{10}$)N($R_{11}$)$_2$, N($R_{11}$)C(=O)$R_{11}$, N($R_{11}$)C(=S)$R_{11}$, N($R_{11}$)C(=NR$_{10}$)$R_{11}$, N($R_{11}$)C(=O)O$R_{11}$, N($R_{11}$)C(=S)O$R_{11}$, N($R_{11}$)C(=NR$_{10}$)O$R_{11}$, N($R_{11}$)C(=O)N($R_{11}$)$_2$, N($R_{11}$)C(=S)N($R_{11}$)$_2$, or N($R_{11}$)C(=NR$_{10}$)N($R_{11}$)$_2$;

or a pharmaceutically acceptable salt thereof.

10. The method of claim 9, wherein a neuraminidase inhibitor is generated following administration of the compound of formula I, wherein the neuraminidase inhibitor is peramivir, or a pharmaceutically acceptable salt thereof.

11. The method of claim 9, wherein a polymerase inhibitor is generated following administration of the compound of formula I, wherein the polymerase inhibitor is comprised of compound (A)

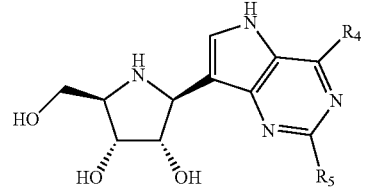

wherein
$R_4$ is NH$_2$; and
$R_5$ is hydrogen;
or a pharmaceutically acceptable salt thereof.

12. The method of claim 9, wherein a neuraminidase inhibitor is generated following administration of the compound of formula I, wherein the neuraminidase inhibitor is peramivir, or a pharmaceutically acceptable salt thereof; and
  a polymerase inhibitor is generated following administration of the compound of formula I, wherein the polymerase inhibitor is comprised of compound (A)

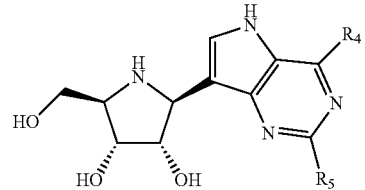

wherein
$R_4$ is NH$_2$; and
$R_5$ is hydrogen; or
a pharmaceutically acceptable salt thereof.

13. The method of claim 9, wherein the compound of formula I is

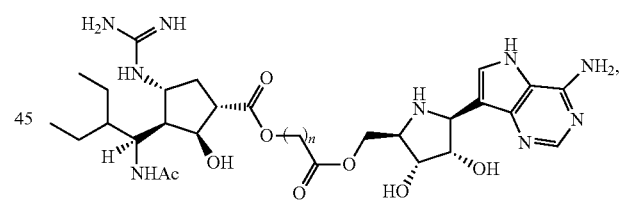

wherein n is an integer from 1 to 6; or a pharmaceutically acceptable salt thereof.

14. The method of claim 9, wherein the compound of formula I is

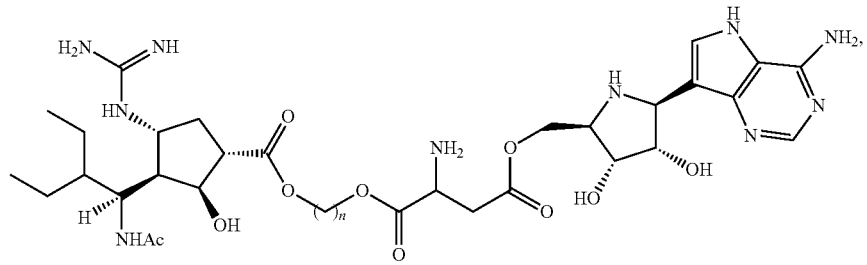

wherein n is an integer from 1 to 6; or a pharmaceutically acceptable salt thereof.

15. The method of claim 9, wherein the compound of formula I is

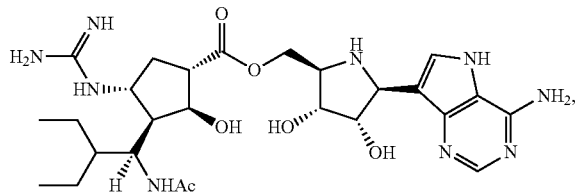 [SMILES: CCC(CC)[C@H](NC(C)=O)[C@@H]1[C@H](O)[C@@H](C(=O)OC[C@H]2N[C@@H](c3c[nH]c4c(N)ncnc34)[C@H](O)[C@@H]2O)C[C@H]1NC(=N)N]

or a pharmaceutically acceptable salt thereof.

16. The method of claim 9, wherein the viral infection is influenza.

17. The method of claim 9, further comprising administering to the subject an effective amount of an additional anti-viral agent.

18. The method of claim 17, wherein the additional anti-viral agent is rimantadine or amantadine.

19. The method of claim 9, wherein the compound of formula I is administered orally.

20. The method of claim 9, wherein the compound of formula I is administered intravenously.

21. The method of claim 9, wherein the compound of formula I is administered intramuscularly.

22. The method of claim 9, wherein the subject is a mammal.

23. The method of claim 9, wherein the subject is a human.

24. The method of claim 9, wherein the subject is an avian.

* * * * *